(12) United States Patent
Kim et al.

(10) Patent No.: US 10,816,800 B2
(45) Date of Patent: Oct. 27, 2020

(54) ELECTRONIC DEVICE AND METHOD OF CONTROLLING THE SAME

(71) Applicant: SAMSUNG ELECTRONICS CO., LTD., Suwon-si, Gyeonggi-do (KR)

(72) Inventors: Jae-deok Kim, Ansan-si (KR); Young-bin Shin, Suwon-si (KR)

(73) Assignee: SAMSUNG ELECTRONICS CO., LTD., Suwon-si, Gyeonggi-do (KR)

( * ) Notice: Subject to any disclaimer, the term of this patent is extended or adjusted under 35 U.S.C. 154(b) by 9 days.

(21) Appl. No.: 15/852,273

(22) Filed: Dec. 22, 2017

(65) Prior Publication Data

US 2018/0180891 A1 Jun. 28, 2018

(30) Foreign Application Priority Data

Dec. 23, 2016 (KR) .................. 10-2016-0177343
Oct. 17, 2017 (KR) .................. 10-2017-0134610

(51) Int. Cl.
| | | |
|---|---|---|
| G02B 27/01 | (2006.01) | |
| A61B 3/00 | (2006.01) | |
| A61B 3/113 | (2006.01) | |
| A61B 3/08 | (2006.01) | |
| A61B 5/16 | (2006.01) | |

(Continued)

(52) U.S. Cl.
CPC ........ G02B 27/0172 (2013.01); A61B 3/0025 (2013.01); A61B 3/0041 (2013.01); A61B 3/0058 (2013.01); A61B 3/085 (2013.01); A61B 3/113 (2013.01); A61B 3/145 (2013.01); A61B 5/165 (2013.01); A61B 5/168 (2013.01); A61B 5/7267 (2013.01); A61B 5/7282 (2013.01);

(Continued)

(58) Field of Classification Search
CPC .............. G02B 27/01; G02B 27/0101; G02B 27/0172; G02B 2027/014; G02B 2027/0178; G02B 27/017
See application file for complete search history.

(56) References Cited

U.S. PATENT DOCUMENTS 3,542,457 A * 11/1970 Ziegler .................. A61B 3/113
351/206
5,159,361 A * 10/1992 Cambier ................ A61B 3/107
351/212

(Continued)

FOREIGN PATENT DOCUMENTS

| KR | 10-2014-0020338 | 2/2014 |
| WO | 2015/081325 | 6/2015 |

(Continued)

OTHER PUBLICATIONS

Search Report and Written Opinion dated Apr. 11, 2018 in counterpart International Patent Application No. PCT/KR2017/015391.

*Primary Examiner* — Olga V Merkoulova
(74) *Attorney, Agent, or Firm* — Nixon & Vanderhye, P.C.

(57) ABSTRACT

An example method of controlling an electronic device worn by a user includes constructing a user model by training a content feature according to response characteristics of an eye of a user who wears the electronic device, and in response to a content feature stored in the user model being detected from reproduced content during content reproduction, processing the reproduced content based on response characteristics of the eye of the user corresponding to the detected content feature.

18 Claims, 19 Drawing Sheets

(51) Int. Cl.
   *A61B 5/00*   (2006.01)
   *A61B 3/14*   (2006.01)
(52) U.S. Cl.
   CPC .... *G02B 27/017* (2013.01); *G02B 2027/0187* (2013.01)

(56) References Cited

U.S. PATENT DOCUMENTS

| | | | | |
|---|---|---|---|---|
| 5,481,622 A * | 1/1996 | Gerhardt | ................ | A61B 3/113 345/158 |
| 5,886,739 A * | 3/1999 | Winningstad | .......... | H04N 7/185 348/115 |
| 6,003,991 A * | 12/1999 | Viirre | .................... | A61B 3/145 351/206 |
| 6,657,673 B2 * | 12/2003 | Ishikawa | ................ | H04N 5/232 348/151 |
| 6,694,482 B1 * | 2/2004 | Arellano | ................. | G06F 16/40 715/251 |
| 7,328,216 B2 * | 2/2008 | Hofmann | ............... | G06F 16/335 |
| 7,483,485 B2 * | 1/2009 | Winningstad | ........... | H04M 1/05 375/240.01 |
| 7,496,140 B2 * | 2/2009 | Winningstad | ........ | G11B 27/034 375/240.01 |
| 7,657,062 B2 * | 2/2010 | Pilu | ........................ | A61B 3/113 345/8 |
| 7,800,650 B1 * | 9/2010 | Prieto | ................... | G02B 27/017 345/8 |
| 8,330,812 B2 * | 12/2012 | Maguire, Jr. | ............ | G06F 3/011 345/679 |
| 8,526,779 B2 * | 9/2013 | Simmons | ........... | H04N 21/4788 348/231.99 |
| 8,573,866 B2 * | 11/2013 | Bond | ..................... | G03B 17/54 348/77 |
| 8,593,570 B2 * | 11/2013 | Boland | .............. | H04N 5/23203 348/376 |
| 9,160,906 B2 * | 10/2015 | Bond | .................... | G02B 27/017 |
| 2005/0083248 A1 * | 4/2005 | Biocca | .............. | G02B 27/0172 345/8 |
| 2007/0173266 A1 * | 7/2007 | Barnes, Jr. | ......... | G06Q 30/0255 455/456.1 |
| 2008/0055194 A1 * | 3/2008 | Baudino | ................. | G06F 3/011 345/8 |
| 2009/0322881 A1 * | 12/2009 | Shu | ................... | G08B 13/19608 348/148 |
| 2012/0256967 A1 | 10/2012 | Baldwin et al. | | |
| 2013/0077049 A1 * | 3/2013 | Bohn | ....................... | G02B 5/20 351/210 |
| 2013/0176533 A1 * | 7/2013 | Raffle | .................... | A61B 3/113 351/209 |
| 2014/0354514 A1 * | 12/2014 | Aronsson | ................ | G06F 3/013 345/7 |
| 2014/0361957 A1 * | 12/2014 | Hua | ........................ | G06F 3/013 345/8 |
| 2015/0002373 A1 | 1/2015 | Kobayashi et al. | | |
| 2015/0379892 A1 | 12/2015 | Sako et al. | | |
| 2016/0210407 A1 * | 7/2016 | Hwang | ................... | G06Q 50/22 |
| 2016/0270656 A1 | 9/2016 | Samec et al. | | |
| 2016/0271002 A9 | 9/2016 | Simmons | | |

FOREIGN PATENT DOCUMENTS

| | | |
|---|---|---|
| WO | 2015/175325 | 11/2015 |
| WO | 2016/078911 | 5/2016 |

* cited by examiner

ELECTRONIC DEVICE AND METHOD OF CONTROLLING THE SAME

CROSS-REFERENCE TO RELATED APPLICATIONS

This application is based on and claims priority from Korean Patent Application Nos. 10-2016-0177343 and 10-2017-0134610, filed on Dec. 23, 2016 and Oct. 17, 2017, respectively, in the Korean Intellectual Property Office, the contents of each of which are incorporated by reference herein in their entirety.

BACKGROUND

Technical Field

The present disclosure generally relates to an electronic device and a method of controlling the same, and more particularly, to an electronic device and a method of controlling the same for learning (or training) a content feature according to response characteristics of a user eye to control reproduction of content reproduced according to the content feature.

In addition, the present disclosure relates to an artificial intelligence (AI) system and an application technology thereof for imitating a function of recognition and determination of a human brain using a machine learning algorithm such as deep learning.

Description of Related Art

Recently, electronic devices (e.g., a head mounted device (HMD)) worn by a user to provide virtual reality have attracted much attention. For example, when wearing an HMD, a user may view and enjoy a realistic stereoscopic view in a virtual world that is definitely different from reality. In addition, a user may enjoy an existing two-dimensional (2D)-based game as a more realistic game with a view of 360 degrees. Thus, virtual reality (VR) contents have been introduced starting from game contents and are expected to be used in various fields such as distance education and medical treatment via a service of sharing experience of virtual reality with a remote site.

In the case of such a HMD, user eyes and an electronic device are very close to each other and, thus, a visual stimulus applied to the user eyes according to a change in specific color and specific brightness may be very high. Thereby, fatigue of user eyes is gradually increased and, in a more serious case, there is the possibility that an illness is caused in the user eye.

When a user has a phobia about a specific object (e.g., a knife and a sharp object), if the specific object appears in an image provided by an HMD, the user may go through the inconvenience of viewing an image using the HMD that triggers this phobia.

Recently, artificial intelligence (AI) systems have also been introduced in the image processing field.

An AI system is a computer system for realizing intelligence of a human level and is a system that becomes more intelligent through autonomous learning and determination of a machine different from an existing rule-based smart system. As the AI system is further used, a recognition rate is enhanced and user preference is more accurately understood. Accordingly, existing rule-based smart systems have been gradually replaced with deep learning-based AI systems.

Artificial intelligence (AI) technology is configured with machine learning (deep learning) and element technologies using machine learning.

Machine learning is algorithm technology for autonomously classifying/learning a feature of input data, and element technologies are for imitating a function such as recognition and determination of human brain using a machine learning algorithm such as deep learning. These are configured for technological fields such as linguistic understanding, visual understanding, inference/prediction, knowledge representation, and motion control.

Various fields to which AI technologies are applied are now described. Linguistic understanding is technology for recognizing/processing human languages/characters and includes natural language processing, machine translation, dialogue system, question and answer, voice recognition/synthesis, and so on. Visual understanding is technology for recognizing and processing an object like human visual sense and includes object recognition, object tracking, image search, human recognition, scene understanding, space understanding, image improvement, and so on. Inference and prediction is technology for determining information to acquire logical inference and prediction and knowledge/possibility-based inference, optimization prediction, a preference-based plan, recommendation, and so on. Knowledge representation is technology for automatically processing human experience information to knowledge data and includes knowledge construction (data generation/classification), knowledge management (data use), and so on. Motion control is technology for controlling autonomous driving of a vehicle and motion of a robot and includes motion control (navigation, collision, and driving), manipulation control (behavior control), and so on.

SUMMARY

Example embodiments of the present disclosure may overcome the above disadvantages and other disadvantages not described above. Also, the present disclosure is not required to overcome the disadvantages described above, and an example embodiment of the present disclosure may not overcome any of the problems described above.

The present disclosure provides an example electronic device and an example method of controlling the same for learning a content feature according to response characteristics of a user eye to construct a user model and for reproducing content using the constructed user model.

According to an aspect of the present disclosure, an example method of controlling an electronic device worn by a user to provide an image includes learning a content feature according to response characteristics of an eye of a user who wears the electronic device and constructing a user model, and, in response to a content feature stored in the user model being detected from the reproduced content during content reproduction, processing the reproduced content based on response characteristics of the user eye corresponding to the detected content feature.

According to another aspect of the present disclosure, an example electronic device worn by a user to provide an image includes a display configured to display content, an image capture device (e.g., camera) configured to photograph a user eye, a memory configured to learn a content feature according to response characteristics of an eye of a user who wears the electronic device and to store a constructed user model, and a processor configured to, in response to a content feature stored in the user model being detected from the reproduced content during content reproduction, process the reproduced content based on response characteristics of the user eye corresponding to the detected content feature.

According to the diverse example embodiments of the present disclosure, an image of a content feature expressed as a user negative response may be processed and, thus, the user may view the image more conveniently without stimulation. In addition, disease information of a user eye may be observed and, thus, information on an abnormal state of the user eye may be provided.

Additional and/or other aspects and advantages of the present disclosure will be set forth in part in the description which follows and, in part, will be obvious from the description, or may be learned by practice of the present disclosure.

BRIEF DESCRIPTION OF THE DRAWINGS

The above and/or other aspects, features, and attendant advantages of the present disclosure will be more apparent and readily understood from the following detailed description of certain example embodiments of the present disclosure, taken in conjunction with the accompanying drawings, in which like reference numerals refer to like elements, and wherein.

DETAILED DESCRIPTION

The present disclosure will now be described more fully with reference to the accompanying drawings, in which example embodiments of the present disclosure are shown. In the following description of the present disclosure, a detailed description of known functions and configurations will be omitted when it may make the subject matter of the present disclosure unclear. The terms used in the specification are defined in consideration of functions used in the present disclosure, and can be changed according to the intent or conventionally used methods of clients, operators, and users. Accordingly, definitions of the terms should be understood on the basis of the entire description of the present disclosure.

It will be understood that, although the terms first, second, third etc. may be used herein to describe various elements, these elements should not be limited by these terms. These terms are only used to distinguish one element from another element. For example, a first element may be termed a second element and a second element may be termed a first element without departing from the teachings of the present disclosure. As used herein, the term "and/or" includes any and all combinations of one or more of the associated listed items.

The terminology used herein is for the purpose of describing particular example embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising" used herein specify the presence of stated features, integers, steps, operations, members, components, and/or groups thereof, but do not preclude the presence or addition of one or more other features, integers, steps, operations, members, components, and/or groups thereof.

In example embodiments of the present disclosure, terms such as "unit", "module", etc. used in the specification may refer to units for processing at least one function or operation, which may be implemented by hardware, software, or a combination thereof. In addition, a plurality of 'modules' or a plurality of 'units' may be integrated into at least one module to be embodied as at least one processor except for a 'module' or a 'unit' that needs to be embodied as specific hardware.

Figure 1A:
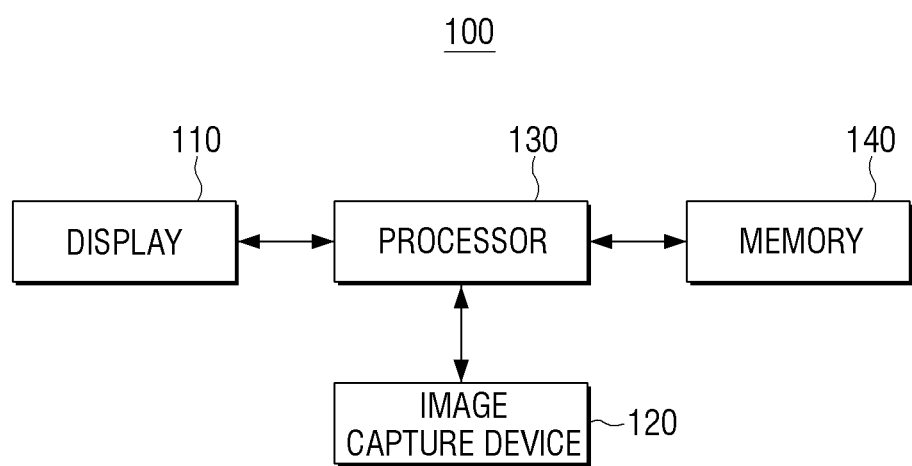
FIGS. 1A and 1B are schematic block diagrams showing a configuration of an electronic device according to an example embodiment of the present disclosure.
Figure 1B:
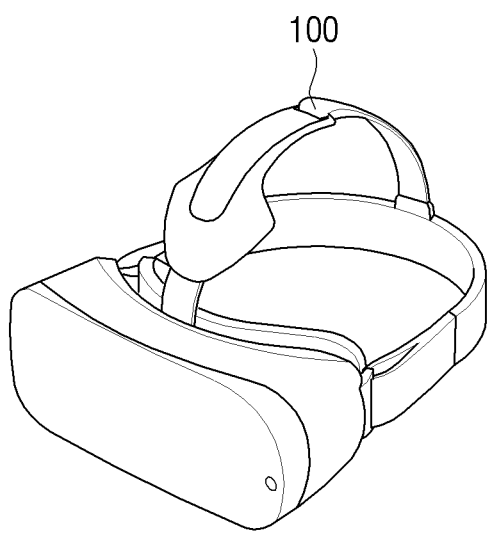

Hereinafter, the present disclosure will be described in detail with reference to the accompanying drawings. FIG. 1A is a schematic block diagram showing a configuration of an electronic device 100 according to an example embodiment of the present disclosure. As shown in FIG. 1A, the electronic device 100 may include a display 110, an image capture device (e.g., camera) 120, a processor 130, and a memory 140. In this case, as shown in FIG. 1B, the electronic device 100 may be a head-up display (HUD) that is worn by a user head to provide an image, but this is merely an example embodiment of the present disclosure and the electronic device 100 may be implemented as other types of electronic devices (e.g., a smartphone, a tablet personal computer (PC), a notebook PC, and the like).

The display 110 may display an image. In particular, the display 110 may display an image(s) acquired from various sources as 3D image(s). In this case, when a user wears the electronic device 100, the display 110 may be positioned on an internal surface of the electronic device 100, which is viewed by a user's eyes. Accordingly, the display 110 may provide a stereoscopic image with a high sense of immersion to a user who wears the electronic device 100.

The image capture device (e.g., camera) 120 may photograph a user's eyes. In particular, the image capture device 120 may be positioned on the internal surface of the electronic device 100 to photograph the user eyes.

The memory 140 may store various data and programs for control of the electronic device 100. In particular, the memory 140 may store a user model constructed by learning a content feature according to response characteristics of the user's eyes photographed by the image capture device 120.

The processor 130 may control an overall operation of the electronic device 100. Detecting the content feature stored in the user model from reproduced content during reproduction of the content, the processor 130 may process the reproduced content based on the response characteristics of the eyes of a user corresponding to the detected content feature.

In detail, the processor 130 may learn a content feature according to the response characteristics of the user's eyes photographed by the image capture device 120 to construct the user model. In this case, the response characteristics of the user's eyes may be a feature of a shape, size, and color change of a user eye or reaction velocity of a user eye and may include without limitation eye blink, eye closure, eye frown, pupil dilation, pupil contraction, and the like.

In more detail, the processor 130 may capture an image containing an eye(s) of a user who wears the electronic device 100 through the image capture device 120 while learned content is reproduced. Upon detecting predetermined response characteristics of the user's eye(s) included in the captured image, the processor 130 may acquire a content feature included on a content frame within a predetermined content section from a time point at which the predetermined response characteristics are detected. The processor 130 may learn predetermined response characteristics and a content feature to construct the user model. In this case, the content feature may be at least one of an object (e.g., a knife and a ghost) included in the content frame within the predetermined content section from a time point at which the predetermined response characteristics are detected, a brightness change in the content frame, or a color change in the content frame. The constructed user model may store the predetermined response characteristics corresponding to the content feature.

The processor 130 may process an image of content based on the constructed user model.

In detail, the processor 130 may be configured to analyze reproduced content during content reproduction to determine whether a content feature stored in the user model is present. When a first content feature stored in the user model is present in the reproduced content, the processor 130 may process of an image corresponding to a content frame including the first content feature based on the first content feature and response characteristics corresponding to the first content feature.

According to an example embodiment of the present disclosure, when the first content feature is a specific object and response characteristics of the specific object are a negative response (e.g., eye blink, eye closure, and/or eye frown), the processor 130 may perform filtering processing on the object included in the content or may perform smoothing processing. According to another example embodiment of the present disclosure, when the first content feature is a specific brightness change and a user response to the specific brightness change is negative, the processor 130 may adjust a variation amount of the specific brightness change. According to another example embodiment of the present disclosure, when the first content feature is a specific color change and a user response to the specific color change is negative, the processor 130 may adjust a saturation value of the specific color change.

Upon determining that a user response to a second content feature of the learned user model is positive, the processor 130 may acquire a keyword of a content feature and may control the display 110 to provide a list including a determined recommendation content based on the acquired keyword in response to a user command.

The processor 130 may cumulatively store the captured image including a user's eye(s) in the memory 140 and may analyze the stored images including the user's eye(s) to determine an abnormal state of the user's eye(s). Upon determining that the user's eye(s) is abnormal, the processor 130 may control the display 110 to provide information on the abnormal state.

Figure 2:
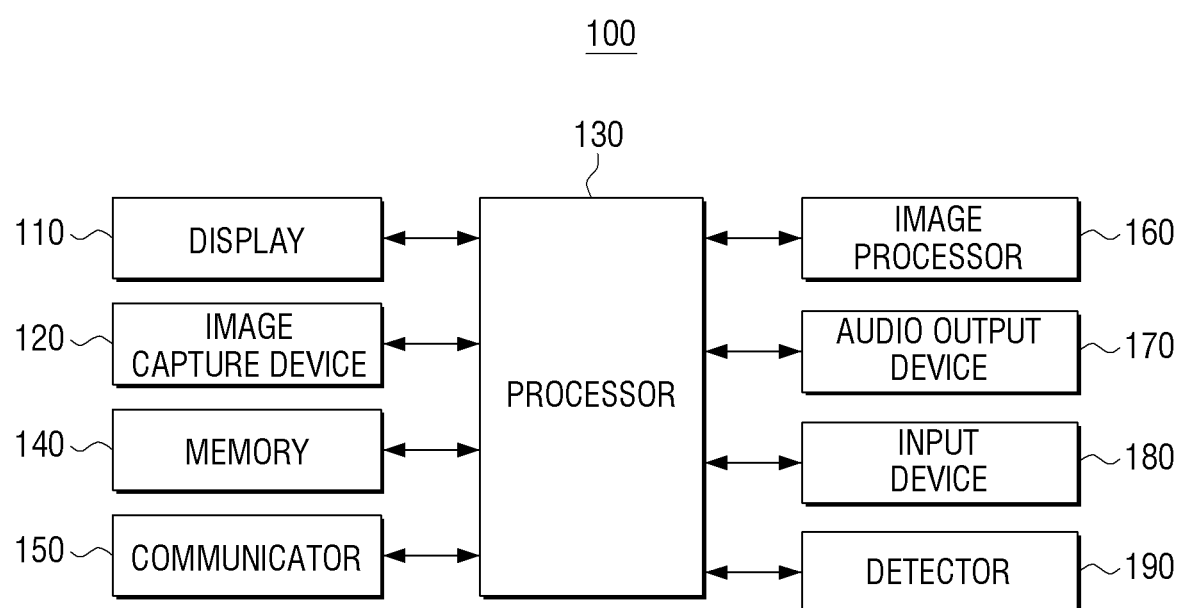
FIG. 2 is a block diagram showing a configuration of an electronic device in detail according to an example embodiment of the present disclosure.

FIG. 2 is a block diagram showing a configuration of the electronic device 100 in detail according to an example embodiment of the present disclosure. As shown in FIG. 2, the electronic device 100 may include the display 110, the image capture device 120, the memory 140, a communicator (e.g., including communication circuitry) 150, an image processor 160, an audio output device (e.g., including audio output circuitry) 170, an input device (e.g., including input circuitry) 180, a detector 190, and the processor 130.

The display 110 may display various image content, information, a user interface (UI), etc. provided by the electronic device 100. For example, the display 110 may display various execution images of a navigation application.

For example, the display 110 may display an image(s) acquired from various sources as 3D image(s). In particular, the display 110 may display a left-eye image through a display corresponding to a left eye of a user and may display a right-eye image through a display corresponding to a right eye of the user to display a 3D image.

In this case, when the user wears the electronic device 100, the display 110 may be positioned on the internal surface of the electronic device 100, which is viewed by the user. Accordingly, the display 110 may provide a stereoscopic image with a high sense of immersion to a user who wears the electronic device 100.

When the user wears the electronic device 100, the image capture device (e.g., including a camera) 120 may be positioned on the internal surface of the electronic device 100 to photograph a user's eye(s). In this case, the image capture device 120 may be a general-purpose camera, but this is merely an example embodiment and the image capture device 120 may also be implemented with or as an infrared camera or the like.

The memory 140 may store various programs and data required for an operation of the electronic device 100. The memory 140 may be implemented as a non-volatile memory, a volatile memory, a flash memory, a hard disk drive (HDD), a solid state drive (SSD), and/or the like. The memory 140 may be accessed by the processor 130 and the processor 130 may read/record/correct/delete/update data. In the present disclosure, the term 'memory' may include the memory 140, ROM (not shown) and/or RAM (not shown) in the processor 130, and/or a memory card (not shown) (e.g., a micro SD card and a memory stick) installed in the electronic device 100.

The memory 140 may store a program, data, and the like for configuring various images to be displayed on a display region of the display 110. The memory 140 may store the user model for storing a content feature corresponding to response characteristics of a user's eye(s) according to an example embodiment of the present disclosure.

The communicator (e.g., including communication circuitry) 150 may communicate with various types of external devices using various types of communication methods. The communicator 150 may include at least one of a WiFi chip, a Bluetooth chip, a wireless communication chip, or an NFC chip. The processor 130 may communicate with an external server or various external devices using the communicator 150.

In particular, the communicator 150 may communicate with an external electronic device (e.g., a smartphone, a navigation device, and a server). For example, the communicator 150 may receive image content from an external electronic device.

The image processor 160 may process an image(s) of image data received from various sources. The image processor 160 may perform various image processing such as decoding, scaling, noise filtering, frame rate conversion, and resolution conversion on the image data.

The audio output device (e.g., including a speaker and associated audio output circuitry) 170 may output various alarms or voice messages as well as various audio data processed by an audio processing module.

The input device (e.g., including input circuitry) 180 may accept input of a user command for manipulating the electronic device 100 and may transmit information on the user command to the processor 130. In particular, the input device 180 may be a button (e.g., a physical button, an optical key, or a keypad) included in the electronic device 100, but this is merely an example embodiment and the input device 180 may be implemented using additional or alternative input devices.

For example, the input device 180 may be implemented as a touch panel, a (digital) pen sensor, etc. for detecting a user touch. The touch panel may use at least one of, for example, a capacitive method, a resistive method, an infrared method, or an ultrasonic method. The touch panel may further include a tactile layer to provide a tactile response to a user. The (digital) sensor may be, for example, a portion of a touch panel or may include a separate element.

As noted, the input device 180 may be implemented as a button, touch panel, a pen sensor, or the like but these are merely example embodiments and the input device 180 may be implemented as various electronic devices such as a microphone for receiving user speed, a camera for photographing a user motion, and a pointing device.

The detector 190 may include various sensors for detecting a state of the electronic device 100. In particular, the detector 190 may include a GPS sensor for detecting a position of the electronic device 100, a motion sensor (e.g., an acceleration sensor, a gyro sensor, and an electromagnetic sensor) for detecting a motion of the electronic device 100, a camera sensor for photographing a path of vehicle driving, and so on.

The processor 130 may be electrically connected to various components (e.g., the display 110, the memory 140, and the image capture device 120) of the electronic device 100 to control an overall operation and function of the electronic device 100. In particular, the processor 130 may control an overall operation of the electronic device 100 using various programs stored in the memory 140.

Figure 3:
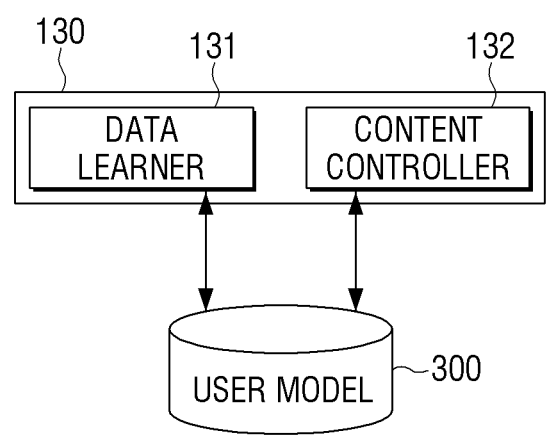
FIG. 3 is a block diagram showing a configuration of a processor included in an electronic device according to an example embodiment of the present disclosure.

In detail, as shown in FIG. 3, the processor 130 may include a data learner 131 for generating a user model 300 and a content controller 132 for processing content using the user model 300.

The data learner 131 may learn response characteristics of a user's eye(s) for a content feature. In particular, the data learner 131 may learn a content feature of a response of the user eye based on an image of the user eye and the learning content. In this case, the data learner 131 may learn whether a user expresses specific response characteristics with respect to a specific content feature to construct the user model 300 for storing a content feature according to response characteristics of the user's eye(s).

The content controller 132 may process reproduced content based on the user model 300 generated by the data learner 131. In detail, upon detecting a content feature stored in the user model 300, the content controller 132 may process an image(s) of content based on response characteristics of a user's eye(s) corresponding to the detected content feature.

At least one of the data learner 131 and the content controller 132 may be manufactured in the form of at least one hardware chip and may be installed in the electronic device 100. For example, at least one of the data learner 131 and the content controller 132 may be manufactured in the form of a dedicated hardware chip for artificial intelligence (AI) or may be manufactured as a part of an existing general-purpose processor (e.g., a CPU or an application processor) or a graphic dedicated processor (e.g., a GPU) and may be installed in the aforementioned various electronic devices 100.

In this case, the data learner 131 and the content controller 132 may be installed in one electronic device 100 or may be installed in separate electronic devices, respectively. For example, one of the data learner 131 and the content controller 132 may be included in an electronic device and the other one may be included in an external portable terminal (e.g., a smartphone) or server. The data learner 131 may provide model information constructed by the data learner 131 to the content controller 132 by wire or wirelessly.

At least one of the data learner 131 and the content controller 132 may be implemented as a software module. When at least one of the data learner 131 and the content controller 132 is implemented as a software module (or a program module including an instruction), the software module may be stored in a non-transitory computer readable medium (or media). In this case, at least one software module may be provided by an operating system (OS) or may be provided by a predetermined application. Alternatively, a portion of at least one software module may be provided by an operating system (OS) and the remaining portion may be provided by a predetermined application.

Hereinafter, with reference to FIGS. 4A, 4B, 5 and 6, the features of the data learner 131 and the content controller 132 will be described in more detail.

Figure 4A:
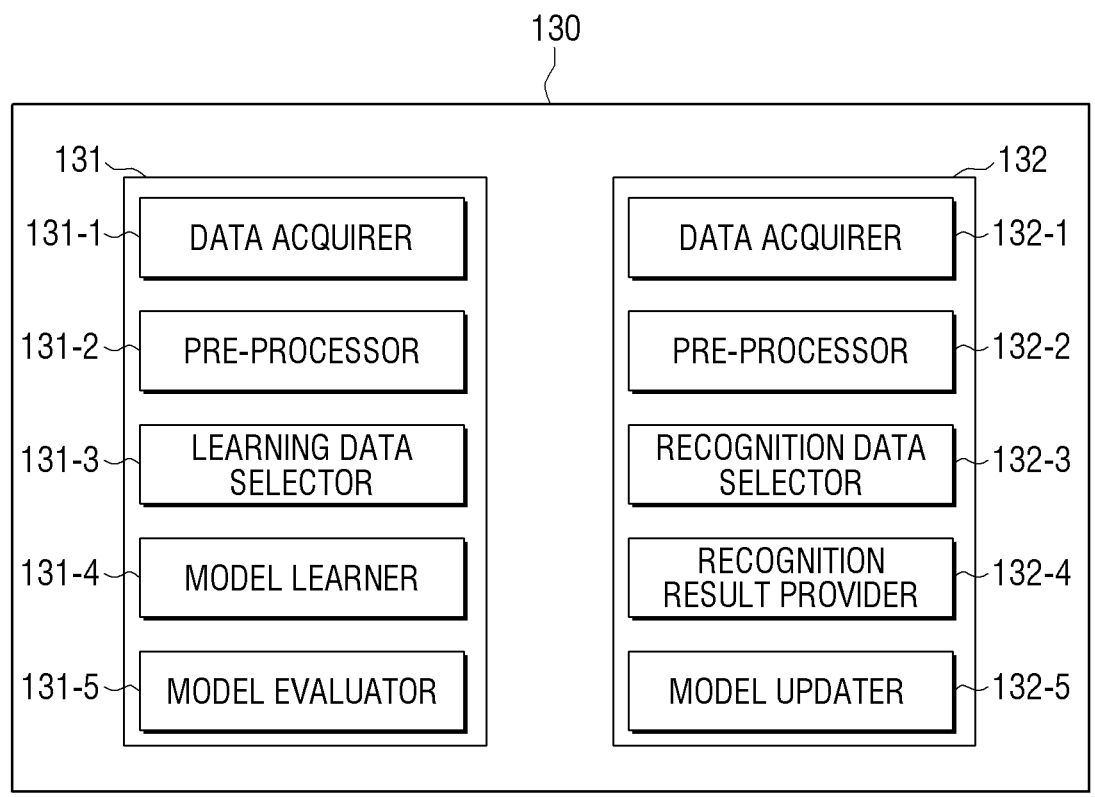
FIG. 4A is a block diagram showing a configuration of a data learner and a content controller included in an electronic device according to an example embodiment of the present disclosure.

Referring to FIG. 4A, the data learner 131 according to some example embodiments of the present disclosure may include a data acquirer 131-1, a pre-processor 131-2, a learning data selector 131-3, a model learner 131-4, and a model evaluator 131-5.

However, the present disclosure is not limited thereto. According to various example embodiments of the present disclosure, the data learner 131 may include all or some of the aforementioned components. For example, the data learner 131 may include only the data acquirer 131-1 and the model learner 131-4. In addition, according to various example embodiments of the present disclosure, the data learner 131 may further include other components in addition to the aforementioned components.

The data acquirer 131-1 may acquire learning data required to analyze a content feature according to response characteristics of a user's eye(s). In this case, the data acquirer 131-1 may acquire image data, content data, etc. including a user's eye(s) photographed by the image capture device 120 as the learning data. In this case, the content data may include audio data and metadata as well as the image data contained in the content data.

The pre-processor 131-2 may pre-process the acquired learning data to use the learning data acquired to analyze a content feature according to response characteristics of a user's eye(s). The pre-processor 131-2 may process the acquired data in a predetermined format to use the learning data acquired for learning for analyzing a content feature according to response characteristics of a user's eye(s) by the model learner 131-4 that will be described below.

The learning data selector 131-3 may select learning data required for learning from the pre-processed learning data. The selected learning data may be provided to the model learner 131-4. The learning data selector 131-3 may select the learning data required for learning from the pre-processed learning data according to a predetermined standard for analysis of a content feature according to response characteristics of a user's eye(s). For example, the learning data selector 131-3 may use, as learning data, only image data including response characteristics of a predetermined eye of a user.

However, the learning data selector 131-3 may select some learning data from the pre-processed learning data, but this is merely an example embodiment and, thus, the learning data selector 131-3 may select all of the pre-processed learning data. The learning data selector 131-3 may select learning data prior to a pre-processing operation by the pre-processor 131-2.

The model learner 131-4 may learn a content feature according to response characteristics of a user's eye(s) based on the learning data to construct a user model. In this case, the model learner 131-4 may analyze the content feature according to the response characteristics of the user's eye(s) and may learn an cumulative analysis result to construct the user model. In this case, the user model may store response characteristics of a user's eye(s) and a content feature that are matched with each other. A method of constructing a user model using learning data by the model learner 131-4 will be described in more detail with reference to FIG. 5.

The model learner 131-4 may make the user model, used to analyze a content feature according to response characteristics of a user's eye(s), learn using learning data. In this case, the user model may be a pre-constructed model. For example, the user model may be a model that is pre-constructed by receiving basic learning data (e.g., general response characteristics of a user's eye(s) and a general content feature).

The user model may be constructed in consideration of an application field of data analysis, a purpose of learning, or computer performance of a device. The user model may be, for example, a model based on a neutral network. For example, a model, such as a deep neural network (DNN), a recurrent neural network (RNN), and a bidirectional recurrent deep neural network (BRDNN), may be used as the user model, but the present disclosure is not limited in this respect.

According to various example embodiments of the present disclosure, when a plurality of pre-constructed user models are present, the model learner 131-4 may determine a user model with a high relationship between input learning data and basic learning data as a user model as a learning target. In this case, the basic learning data may be pre-classified for each data type and the user model may be pre-constructed for each data type. For example, the basic learning data may be pre-classified based on various references such as a generator of the learning data, a generation time of the learning data, a size of the learning data, a genre of the learning data, an object type in the learning data, and so on.

The model learner 131-4 may make the user model learn using a learning algorithm including, for example, error back-propagation or gradient descent.

The model learner 131-4 may make the user model learn through, for example, supervised learning using learning data as an input value. The model learner 131-4 may make the user model learn through, for example, unsupervised learning for autonomously learning a type of data required to analyze a content feature according to response characteristics of a user's eye(s) without particular supervision to discover a reference for analysis of a user driving history. The model learner 131-4 may make the user model to learn through, for example, reinforcement learning using feedback about whether a result of a user's driving history according to learning is accurate.

When the user model is learned, the model learner 131-4 may store the learned user model. In this case, the model learner 131-4 may store the learned user model in the memory 140 of the electronic device 100 including the content controller 132. Alternatively or additionally, the model learner 131-4 may store the learned user model in a memory of an external portable terminal or server that is connected to the electronic device 100 by wire or via a wireless network.

In this case, the memory 140 that stores the learned user model may store therewith a command or data related to at least one of other components of the electronic device. The memory 140 may store software and/or a program. The program may include, for example, kernel, middleware, an application programming interface (API), and/or an application program (or "application"), etc.

The model evaluator 131-5 may input evaluation data to the user model and, when an analysis result output from the evaluation data does not satisfy a predetermined reference or criteria, the model evaluator 131-5 may make the model learner 131-4 re-learn. In this case, the evaluation data may be predetermined data for evaluation of the user model.

For example, the model evaluator 131-5 may evaluate that the analysis result does not satisfy a predetermined reference or criteria when the number or rate of evaluation data with an inaccurate analysis result exceeds a predetermined threshold value from analysis results of the learned user model with respect to the evaluation data. For example, when the predetermined reference or criteria is defined as a rate of 2%, the learned user model outputs an inaccurate analysis result with respect to evaluation data, the number of which exceeds 20, from a total of 1000 evaluation data, the model evaluator 131-5 may evaluate that the learned user model is not appropriate.

When a plurality of learned user models is present, the model evaluator 131-5 may evaluate whether each learned user model satisfies a predetermined reference or criteria and may determine a model that satisfies the predetermined reference or criteria as a final user model. In this case, when a plurality of models satisfies the predetermined reference or criteria, the model evaluator 131-5 may determine one or a predetermined number of models as the final user model in descending order of an evaluation score.

At least one of the data acquirer 131-1, the pre-processor 131-2, the learning data selector 131-3, the model learner 131-4, and the model evaluator 131-5 in the data learner 131 may be manufactured in the form of at least one hardware chip and may be installed in an electronic device. For example, at least one of the data acquirer 131-1, the pre-processor 131-2, the learning data selector 131-3, the model learner 131-4, and the model evaluator 131-5 may be manufactured in the form of a dedicated hardware chip for artificial intelligence (AI) or may be manufactured as a part of an existing general-purpose processor (e.g., a CPU or an application processor) or a graphic dedicated processor (e.g., a GPU) and may be installed in the aforementioned various electronic devices.

The data acquirer 131-1, the pre-processor 131-2, the learning data selector 131-3, the model learner 131-4, and the model evaluator 131-5 may be installed in the electronic device 100 or may be installed in separate electronic devices, respectively. For example, one or more of the data acquirer 131-1, the pre-processor 131-2, the learning data selector 131-3, the model learner 131-4, and the model evaluator 131-5 may be included in an electronic device and the others may be included in a server.

At least one of the data acquirer 131-1, the pre-processor 131-2, the learning data selector 131-3, the model learner 131-4, and the model evaluator 131-5 may be implemented as a software module. When at least one of the data acquirer 131-1, the pre-processor 131-2, the learning data selector 131-3, the model learner 131-4, and the model evaluator 131-5 is implemented as a software module (or a program module including an instruction), the software module may be stored in a non-transitory computer readable medium (or media). In this case, at least one software module may be provided by an operating system (OS) or may be provided by a predetermined application. Alternatively, a portion of at least one software module may be provided by an operating system (OS) and the remaining portion may be provided by a predetermined application.

FIG. 4A also provides a block diagram of the content controller 132 according to an example embodiment of the present disclosure.

Referring to FIG. 4A, the content controller 132 according to some example embodiments of the present disclosure may include a data acquirer 132-1, a pre-processor 132-2, a recognition data selector 132-3, a recognition result provider 132-4, and a model updater 132-5. However, the present disclosure is not limited thereto. According to various example embodiments of the present disclosure, a data classifier (not shown) may include some of the aforementioned components of the content controller 132. For example, the content controller 132 may include only the data acquirer 132-1 and the recognition result provider 132-4. According to various example embodiments of the present disclosure, the content controller 132 may further include other components in addition to the aforementioned components.

The content controller 132 may estimate whether a content feature is included in content according to a reference for determining whether a user model corresponds to a learned content feature according to response characteristics of a user's eye(s) using at least one user model.

The data acquirer 132-1 may acquire input data required to estimate the content feature according to response characteristics of a user's eye(s). In this case, the data acquirer 132-1 may acquire video data. The video data may be stored in, for example, the memory 140 of the electronic device 100 or may be data received from another electronic device (e.g., a smartphone, a tablet PC, and a server that have established a communication relationship with the electronic device 100 to transmit and receive content).

The pre-processor 132-2 may pre-process the acquired data to use the acquired input data to estimate a content feature. The pre-processor 132-2 may process the acquired data in a predetermined format to use the acquired learning data when the recognition result provider 132-4 that will be described below estimates a content feature of an image.

For example, the pre-processor 132-2 may remove noise of the video data acquired by the data acquirer 132-1 or process the video data to select significant data.

The recognition data selector 132-3 may select data required for learning from the pre-processed input data. The selected data may be provided to the recognition result provider 132-4. To estimate whether a content feature is included in an image(s), the recognition data selector 132-3 may select all or some of the pre-processed data.

The recognition result provider 132-4 may apply the selected input data to a user model to estimate whether a content feature is included in an image. The recognition result provider 132-4 may use the data selected by the recognition data selector 132-3 as an input value to apply the selected data to the user model. The recognition result provider 132-4 may estimate, for example, whether a content feature is included in an image(s) based on a user model corresponding to a predetermined condition among at least one user model. A method of estimating a content feature using input data by the recognition result provider 132-4 will be described in more detail with reference to FIG. 6.

The model updater 132-5 may update a user model based on evaluation of a recognition result provided by the recognition result provider 132-4. For example, the model updater 132-5 may provide an estimation result of a content feature included in an image provided by the recognition result provider 132-4 to the model learner 131-4 and, thus, the model learner 131-4 may update the user model.

At least one of the data acquirer 132-1, the pre-processor 132-2, the recognition data selector 132-3, the recognition result provider 132-4, and the model updater 132-5 in the content controller 132 may be manufactured in the form of at least one hardware chip and may be installed in the electronic device 100. For example, at least one of the data acquirer 132-1, the pre-processor 132-2, the recognition data selector 132-3, the recognition result provider 132-4, and the model updater 132-5 may be manufactured in the form of a dedicated hardware chip for artificial intelligence (AI) or may be manufactured as a part of an existing general-purpose processor (e.g., a CPU or an application processor) or a graphic dedicated processor (e.g., a GPU) and may be installed in the aforementioned various electronic devices.

The data acquirer 132-1, the pre-processor 132-2, the recognition data selector 132-3, the recognition result provider 132-4, and the model updater 132-5 may be installed in one electronic device or may be installed in separate electronic devices, respectively. For example, one or more of the data acquirer 132-1, the pre-processor 132-2, the recognition data selector 132-3, the recognition result provider 132-4, and the model updater 132-5 may be included in the electronic device and the others may be included in a server.

At least one of the data acquirer 132-1, the pre-processor 132-2, the recognition data selector 132-3, the recognition result provider 132-4, and the model updater 132-5 may be implemented as a software module. When at least one of the data acquirer 132-1, the pre-processor 132-2, the recognition data selector 132-3, the recognition result provider 132-4, and the model updater 132-5 is implemented as a software module (or a program module including an instruction), the software module may be stored in a non-transitory computer readable medium (or media). In this case, at least one software module may be provided by an operating system (OS) or may be provided by a predetermined application. Alternatively, a portion of at least one software module may be provided by an operating system (OS) and the remaining portion may be provided by a predetermined application.

Figure 4B:
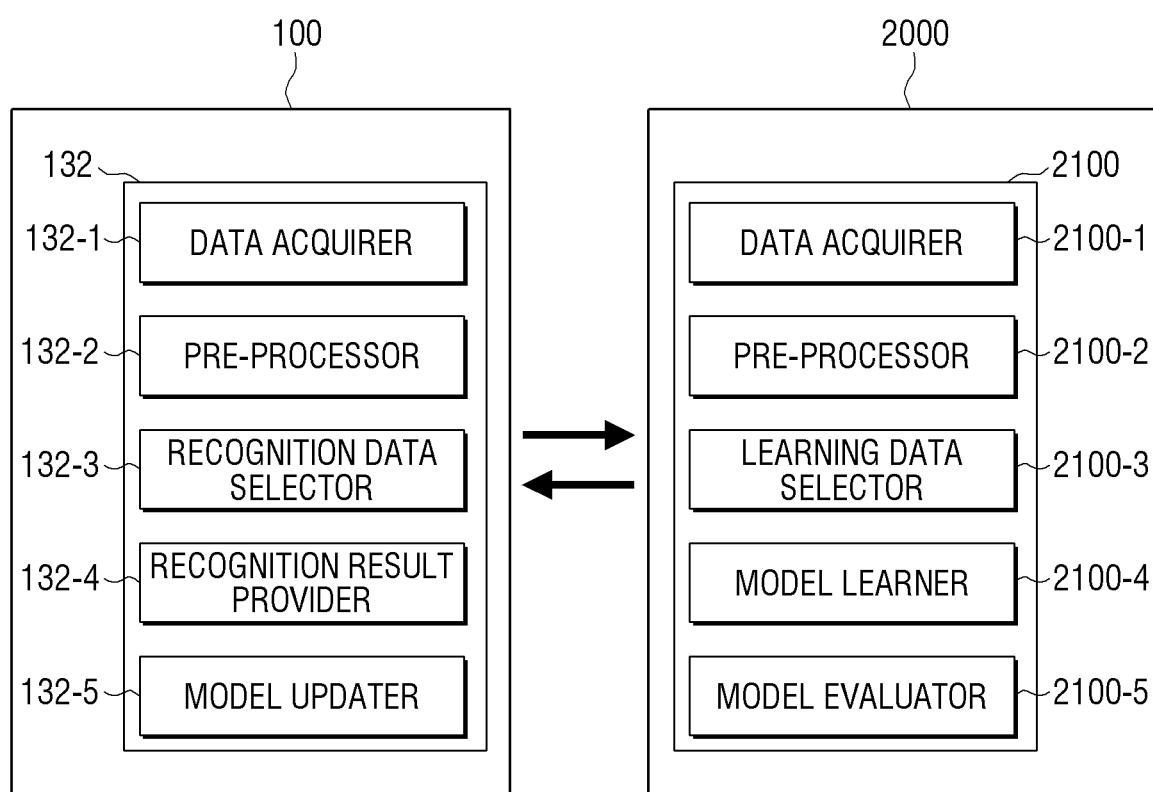
FIG. 4B is a diagram for explanation of an example in which an electronic device and a server are operatively associated to learn and recognize data according to an example embodiment of the present disclosure.

FIG. 4B is a diagram for explanation of an example in which an electronic device and a server are operatively associated with each other to learn and recognize data according to an example embodiment of the present disclosure.

Referring to FIG. 4B, a server 2000 may construct a user model for estimating of a content feature included in an image and a disease prediction model for estimating an abnormal state (e.g., a disease state) of an eye(s). The electronic device 100 may estimate a content feature included in content using the user model constructed by the server 2000 and may estimate an abnormal state of a user eye using the disease prediction model.

In this case, a data learner 2100 of the server 2000 may perform a function of the data learner 131 shown in FIG. 4A. That is, a data acquirer 2100-1, a pre-processor 2100-2, a learning data selector 2100-3, a model learner 2100-4, and a model evaluator 2100-5 included in the data learner 2100 of the server 2000 may correspond to the data acquirer 131-1, the pre-processor 131-2, the learning data selector 131-3, the model learner 131-4, and the model evaluator 131-5 shown in FIG. 4A.

The data learner 2100 of the server 2000 may learn response characteristics of a user's eye(s) with respect to a content feature to estimate a content feature included in a video image. The data learner 2100 may learn whether a user expresses specific response characteristics with respect to a specific content feature and may construct a user model (e.g., the user model 300 of FIG. 3) for storing a content feature according to response characteristics of a user eye.

The data learner 2100 of the server 2000 may learn a disease type according to a state of an eye with a disease related to an eye. The data learner 2100 may learn whether an eye(s) is abnormal (e.g., a disease type) according to a change in an eye state during a predetermined time period to construct a disease prediction model.

The recognition result provider 132-4 of the electronic device 100 may apply data selected by the recognition data selector 132-3 to the user model or the disease prediction model generated by the server 2000 to estimate a content feature or to estimate an abnormal state related to a user's eye(s).

For example, the recognition result provider 132-4 may transmit the input data selected by the recognition data selector 132-3 to the server 2000 and may apply the input data received by the server 2000 to the user model or the disease prediction model to make a request for estimation of a content feature or to make a request for estimation of an abnormal state related to an eye(s). The recognition result provider 132-4 may receive information corresponding to the content feature or the abnormal state related to an eye(s), estimated by the server 2000, from the server 2000.

Figure 5:
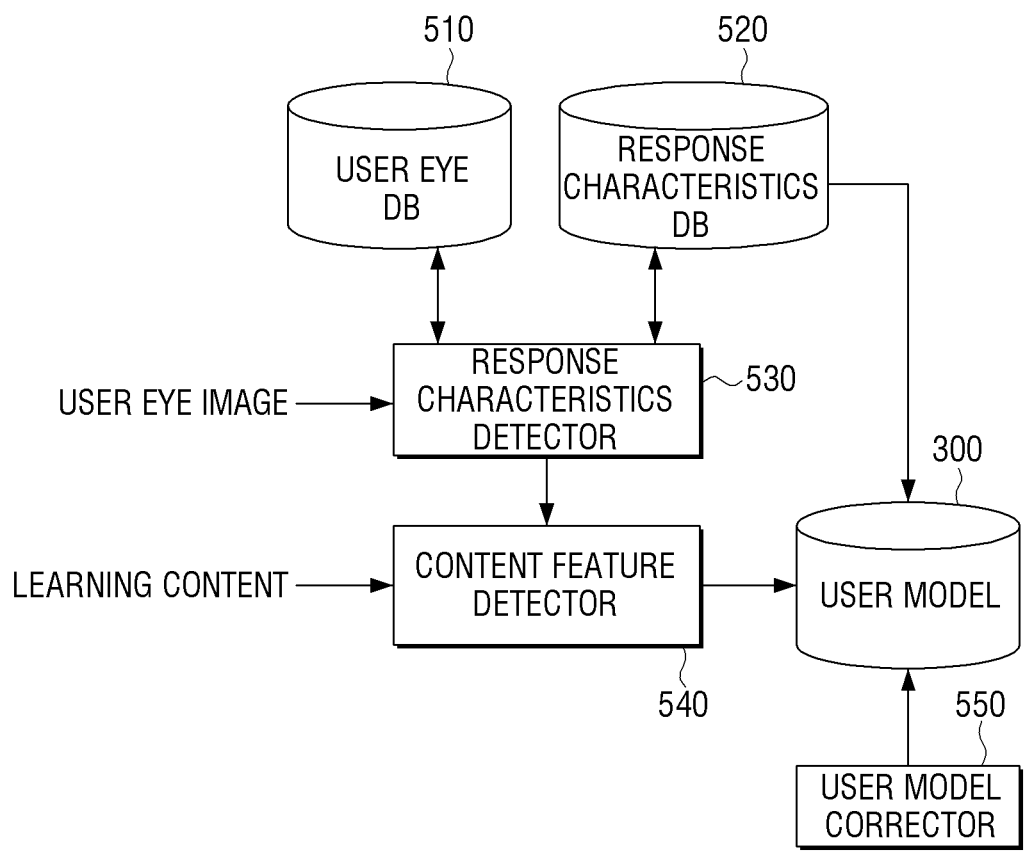
FIG. 5 is a diagram for explanation of a data learner according to an example embodiment of the present disclosure.

FIG. 5 is a diagram for explanation of a method of constructing a user model by the model learner 131-4 according to an example embodiment of the present disclosure. The model learner 131-4 may include a response characteristics detector 530 and a content feature detector 540.

First, the response characteristics detector 530 may acquire image data including a user's eye(s) as learning data. In this case, the response characteristics detector 530 may acquire the image data including a user's eye(s), pre-processed in a predetermined format in real time, but this is merely an example embodiment and the response characteristics detector 530 may acquire only an image data including a user's eye(s) that expresses a feature response.

Since sizes and shapes of eyes are different for respective users, the response characteristics detector 530 may detect a change in shape and size of a user's eye(s) using a user eye database (DB) 510 for storing information on eyes of a user who wears the electronic device 100 and a response characteristics DB 520 for storing information on a response characteristics DB 520 of a general user's eye(s). For example, the response characteristics detector 530 may detect a change in an eye shape (e.g., frown), eye blink, eye closure, pupil dilation, etc. as response characteristics of a user's eye(s).

The content feature detector 540 may acquire learning content. The content feature detector 540 may analyze a content frame within a predetermined content section (e.g., a content section of about one second from a start point at which response characteristics of a user eye is detected) from a time point at which response characteristics of a user's eye(s) are analyzed to detect a content feature. In this case, the content feature detector 540 may detect an object included in a content frame, object, color change, brightness change, and so on as a content feature.

When the content feature detector 540 detects a content feature, the content feature detector 540 may output response characteristics of a user's eye(s) and content feature corresponding thereto to the user model 300. When the content feature detector 540 does not detect a content feature, the response characteristics detector 530 may determine that response characteristics are not a response to content and may remove the detected response characteristics.

The response characteristics detector 530 and the content feature detector 540 may repeatedly perform the aforementioned method to learn content features according to response characteristics of a user's eye(s).

The user model 300 may match the content feature and the response characteristics of the user's eye(s) detected using the aforementioned method. For example, when a user frequently closes his/her eyes in a scene in which blood or a knife is displayed, the user model 300 may store "eye closure" as response characteristics of a user's eye(s) and may store "blood and knife" as the corresponding content feature. As another example, when a user frowns the eyes in scene transition with a brightness change of 100 or more (e.g., increase from 13 to 113), the user model 300 may store "eye frown" as response characteristics of a user eye and may store "increase of brightness of 100" as the corresponding content feature. As another example, when a user blinks his/her eye(s) in an overall red scene, the user model 300 may store "eye blink" as response characteristics of a user's eye(s) and may store "red scene" as the corresponding content feature. As the aforementioned examples, the user model 300 may store the following table.

TABLE 1

| Response characteristics of user eye(s) | content feature |
| --- | --- |
| Eye closure | Blood and knife |
| Eye blink | Increase of brightness of 100 |
| Change in eye shape(frown) | Red scene appearance |

The user model 300 may update the content stored according to the response characteristics and the content feature that are detected by the response characteristics detector 530 and the content feature detector 540. For example, the user model 300 may delete the pre-stored content or may additionally store new content based on the result detected by the response characteristics detector 530 and the content feature detector 540. That is, the electronic device 100 may continuously learn a content feature according to response characteristics of a user's eye(s) to construct a user model that is optimized to a user.

The user model 300 may match and store response characteristics of a user's eye(s) and a content feature corresponding thereto and may also store various pieces of information such as user emotion information (e.g., negative emotion, positive emotion, fear, hatred, and preference), a detection time point, and a number of times of detection.

Figure 7A:
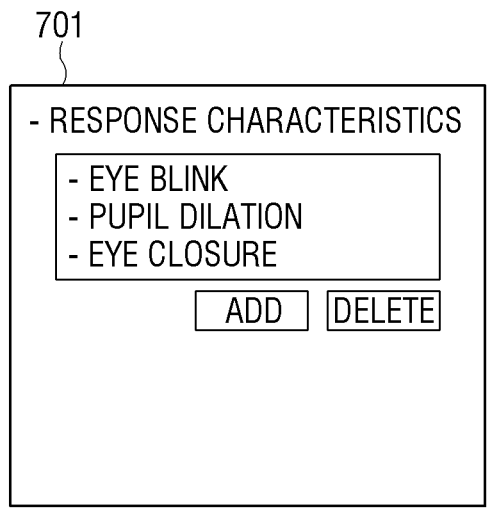
FIGS. 7A and 7B are diagrams for showing a user interface (UI) for correcting a response feature of a user eye and a content feature according to an example embodiment of the present disclosure.
Figure 7B:
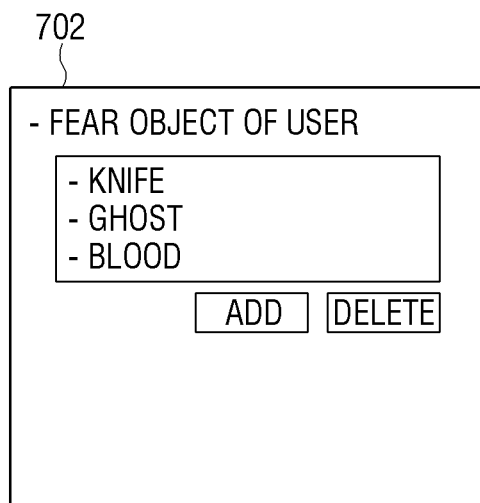

A user model corrector 550 may correct the user model 300 according to a user input. For example, the user model corrector 550 may generate a user interface (UI) for adding/deleting response characteristics of a user's eye(s) and a content feature and may correct the response characteristics of the user's eye(s) and the content feature according to a user input that is input through the UI. For example, as shown in FIG. 7A, the user model corrector 550 may display a UI 701 for adding/deleting the response characteristics of the user's eye(s) and, as shown in FIG. 7B, the user model corrector 550 may display a UI 702 for designating a fear object of a user from a content feature.

In the aforementioned embodiment, a visual content feature and response characteristics of a user's eye(s) are matched and stored but this is merely an example embodiment and other (non-visual) content features (e.g., curse, bomb noise, and noise from Styrofoam) and response characteristics of a user's eye(s) may be matched and stored.

Figure 6:
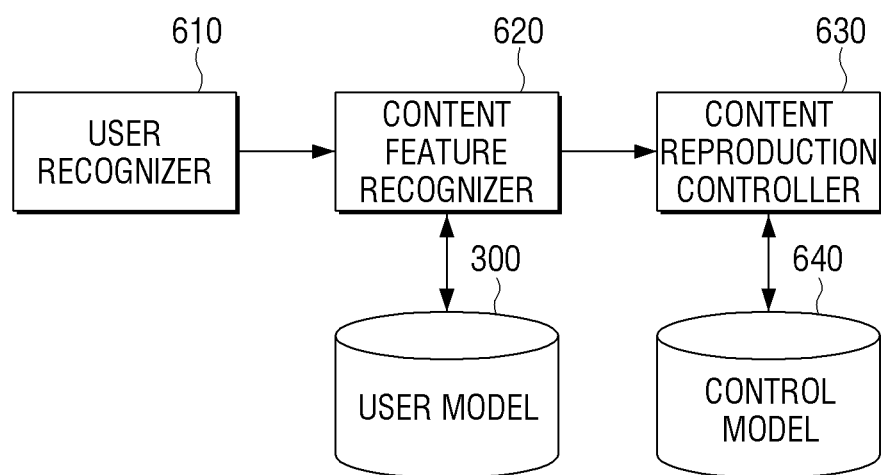
FIG. 6 is a diagram for explanation of a method of processing content by a content controller according to an example embodiment of the present disclosure.

FIG. 6 is a diagram for use in explaining a method of processing content by the recognition result provider 132-4 of the content controller 132 using the user model 300 according to an example embodiment of the present disclosure. According to an example embodiment of the present disclosure, the recognition result provider 132-4 may include a user recognizer 610, a content feature recognizer 620, and a content reproduction controller 630.

First, the user recognizer 610 may recognize a user who wears the electronic device 100. In this case, the user recognizer 610 may photograph a user's iris using the image capture device 120 to recognize the user, but this is merely an example embodiment and the user may be recognized using other methods and techniques (e.g., fingerprint, a password, and voice recognition).

When a user is recognized, the content feature recognizer 620 may analyze whether a content feature stored in the user model 300 is present in reproduced content. In detail, the content feature recognizer 620 may pre-analyze a content frame of a preceding content section from a currently reproduced content frame during reproduction of content to analyze whether a content feature stored in the user model 300 is present. That is, the content feature recognizer 620 may determine whether a specific object is detected, whether a specific color change is detected, and whether a specific brightness change is detected, in a content frame of a preceding content section of a currently reproduced content frame during reproduction of content.

When a content feature stored in the user model 300 is detected by the content feature recognizer 620, the content reproduction controller 630 may process content based on a control model 640. In this case, the control model 640 may match and store response characteristics of a user's eye(s) stored in the user model 300 and a method of processing content according to a content feature.

Figure 8A:
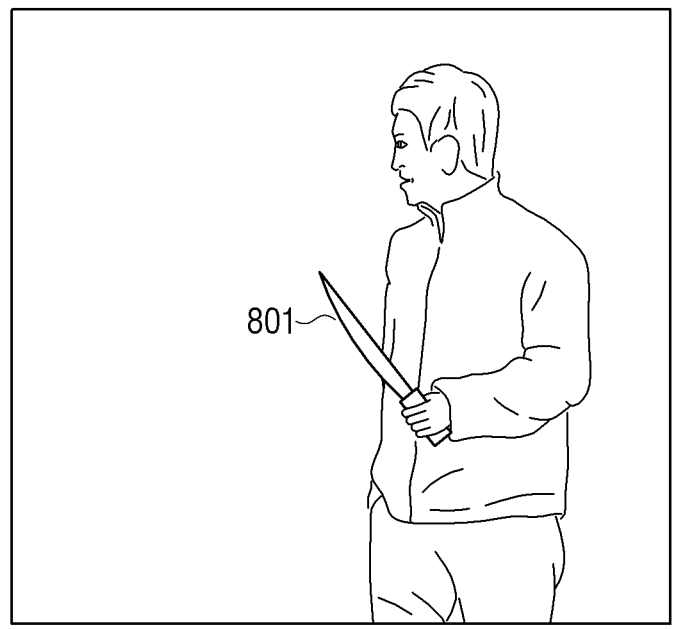
FIGS. 8A and 8B are diagrams for explanation of an example in which an image is processed with respect to an object to which a user has negative emotion according to an example embodiment of the present disclosure.
Figure 8B:
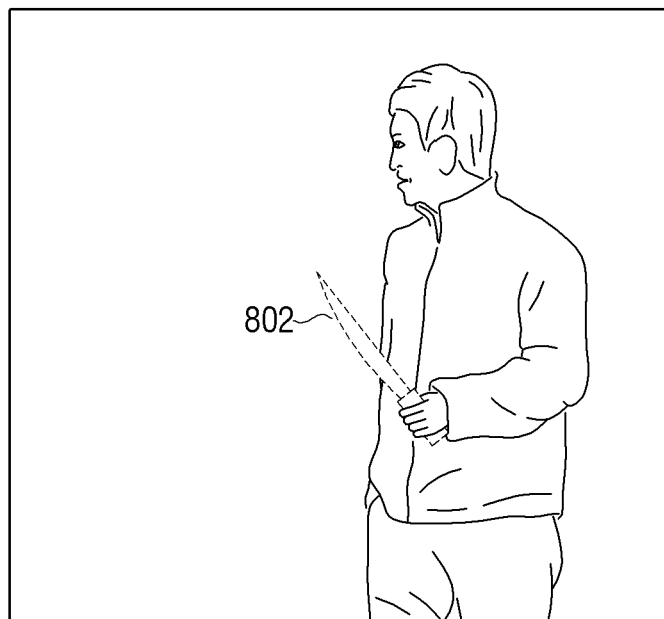

According to an example embodiment of the present disclosure, when a detected content feature is a specific object and response characteristics with respect to the specific object are a negative response (e.g., eye closure), the content reproduction controller 630 may perform filtering processing on the object included in the content or may perform smoothing processing using the control model 640. For example, as shown in FIG. 8A, when a detected content feature is a knife 801 and response characteristics with respect to a knife are eye closure, the content reproduction controller 630 may perform filtering process on a knife region 802 of a content frame, as shown in FIG. 8B.

According to another example embodiment of the present disclosure, when a detected content feature is a specific brightness change and a user response to the specific brightness change is negative (e.g., eye frown), the content reproduction controller 630 may adjust a change amount of the specific brightness change. For example, when the detected content feature is an increase of brightness of 100 and response characteristics with respect to an increase of brightness of 100 is eye frown, the content reproduction controller 630 may reduce a brightness increase value to 70 from 100. In this case, the content reproduction controller 630 may process an image to reduce the brightness increase value but this is merely an example embodiment and the content reproduction controller 630 may control a backlight of the display 110 to reduce the brightness increase value.

According to another example embodiment of the present disclosure, when the detected content feature is a specific color change and a user response to the specific color change is negative (e.g., eye blink), the content reproduction controller 630 may adjust a saturation value of a specific color change. For example, when the detected content feature is a red scene and response characteristics with respect to appearance of a red scene are eye blink, the content reproduction controller 630 may adjust the saturation value to display an orange scene instead of the red scene.

According to the aforementioned example embodiment, the detected content feature is a visual content feature, but this is merely an example embodiment and an acoustic content feature in addition to or alternatively to the visual content feature may also be included in the technological idea of the present disclosure. For example, when "curse" as a content feature and "eye frown" as response characteristics corresponding thereto are stored in the user model 300, curse is detected from reproduced content, the content reproduction controller 630 may process curse on mute and may reproduce content.

In the aforementioned example embodiment, the detected response characteristics of a user's eye(s) are negative, but this is merely an example embodiment and, when response characteristics of a user eye are positive, the positive response characteristics of the user eye and a response characteristics corresponding thereto may be matched and stored in the user model 300. For example, when a user pupil dilates in a scene in which a puppy is displayed, the user model 300 may store "puppy" as a content feature and "pupil dilation" as response characteristics corresponding thereto. In this case, when a user inputs a command for generating a content list in the future, the processor 130 may acquire a keyword (e.g., puppy) from a content feature corresponding to the positive response characteristics and may generate a content list including the content feature based on a keyword.

The processor 130 may continuously photograph a user's eye(s) to check disease information (or health information) of a user eye and may control the display 110 to provide the checked disease information or health-related information.

For example, when a user views a video image using the electronic device 100, the processor 130 may continuously photograph a user's eye(s) to check for an abnormal state of the eye and may provide disease-related information or health-related information.

Figure 9:
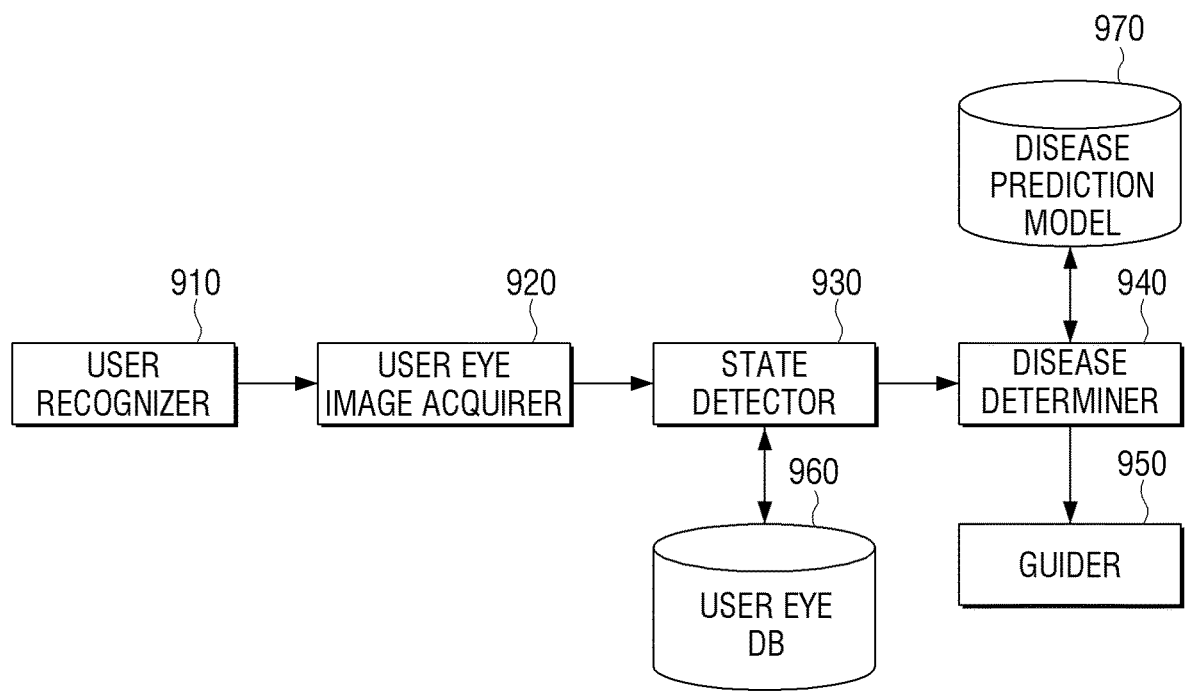
FIG. 9 is a diagram for explanation of an example of determining disease information of a user eye according to an example embodiment of the present disclosure.
Figure 10:
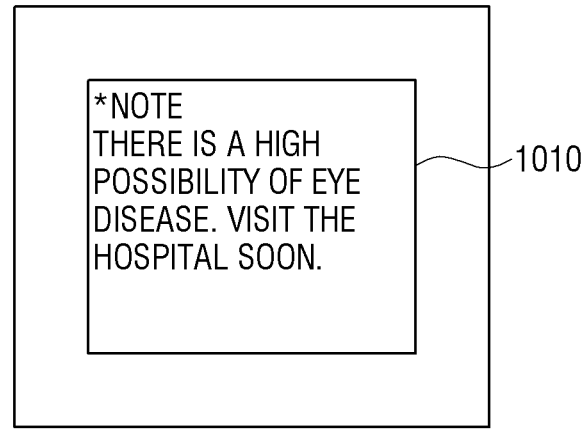
FIG. 10 is a diagram showing a user interface (UI) for guiding disease information of a user eye according to an example embodiment of the present disclosure.

This will be described in more detail with reference to FIGS. 9 and 10. First, to check disease-related information of a user's eye(s), the processor 130 may include a user recognizer 910, a user eye image acquirer 920, a state detector 930, a disease determiner 940, and a guider 950.

The user recognizer 910 may recognize a user based on the captured image of a user's eye(s). In particular, the user recognizer 910 may recognize a user via iris recognition, but this is merely an example embodiment and the user recognizer 910 may recognize a user using other methods.

The user eye image acquirer 920 may acquire image data including a user's eye(s) photographed by the image capture device 120. In this case, the user eye image acquirer 920 may acquire the image data including the user's eye(s), but this is merely an example embodiment and only information on a partial region (e.g., an eye or a pupil) of the image data may be acquired.

The state detector 930 may detect a state of the user's eye(s) included in the image data. In this case, the state detector 930 may detect a change in a size, shape, color, etc. of the user's eye(s) based on a user eye DB 960 that stores a preceding image(s) of a user's eye(s).

According to an example embodiment of the present disclosure, a data learner (e.g., the data learner 2100 of FIG. 4B) may generate disease prediction model 970.

To generate the disease prediction model 970, the data learner (e.g., the data learner 2100 of FIG. 4B) may learn a type of a disease according to a state of an eye(s) having a disease related to an eye(s). In this case, the data learner (e.g., the data learner 2100 of FIG. 4B) for generating the disease prediction model 970 may learn whether an eye(s) is abnormal (e.g., a disease type) according to a change in an eye state during a predetermined time period to construct the disease prediction model 970.

According to an example embodiment of the present disclosure, the disease prediction model 970 may be stored in the server 2000 located outside the electronic device 100. According to various example embodiments of the present disclosure, the electronic device 100 may receive at least a portion of the disease prediction model 970 from the server 2000 and may store the received portion in the memory 140, etc. of the electronic device 100.

The disease determiner 940 may determine whether a disease occurs according to a state of the user's eye(s) detected by the state detector 930 based on the disease prediction model 970. For example, when the state detector 930 detects that a user's eye(s) is inflamed, the disease determiner 940 may determine that iritis occurs.

As another example, when the state detector 930 detects that abnormality occurs in pupil dilation/contraction or response speed is lowered, the disease determiner 940 may determine that Horner syndrome or holmes adie's tonic pupil occurs. As another example, when the state detector 930 detects that pupil movement is abnormal based on head movement, the disease determiner 940 may determine that otolithiasis occurs.

As another example, the disease determiner 940 may determine whether Nystagmus occurs according to eyeball movement. As another example, the disease determiner 940 may detect whether optic nerve is damaged or glaucoma occurs according to whether visual field defect occurs. In this case, the disease determiner 940 may track pupil movement during use of virtual reality (VR) content to generate a visual field map and may determine whether visual field defect occurs through the generated visual field map.

The disease determiner 940 may also determine a disease occurrence prediction time and symptom severity based on a size change, a shape change, a color change, and response speed of an eye (or a pupil) detected by the state detector 930.

When the disease determiner 940 determines that a user's eye(s) has a disease, the guider 950 may provide a guidance message including disease-related information on the user's eye(s). For example, as shown in FIG. 10, the guider 950 may provide a guidance message 1010 such as "There is a high possibility of eye disease. Visit the hospital soon.". In this case, the guidance message may include a disease type, disease occurrence prediction time, disease severity, and so on as well as whether a disease is predicted.

According to an example embodiment of the present disclosure, the electronic device 100 may display a guidance message and/or another electronic device (e.g., a smartphone and a tablet PC) that communicates with the electronic device 100 may display the guidance message.

As such, according to various example embodiments of the present disclosure, a user may also check a health state of an eye while viewing content such as video images using the electronic device 100. In particular, with regard to estimation of an abnormal state related to an eye using the disease prediction model according to the present disclosure, the electronic device 100 may estimate an abnormal state of an eye according to a change in an eye state for a predetermined time (e.g., a time of 1 hour or more) to increase the accuracy of examination and may also reduce a user inconvenience of preparing a separate time for eye examination.

Figure 11:
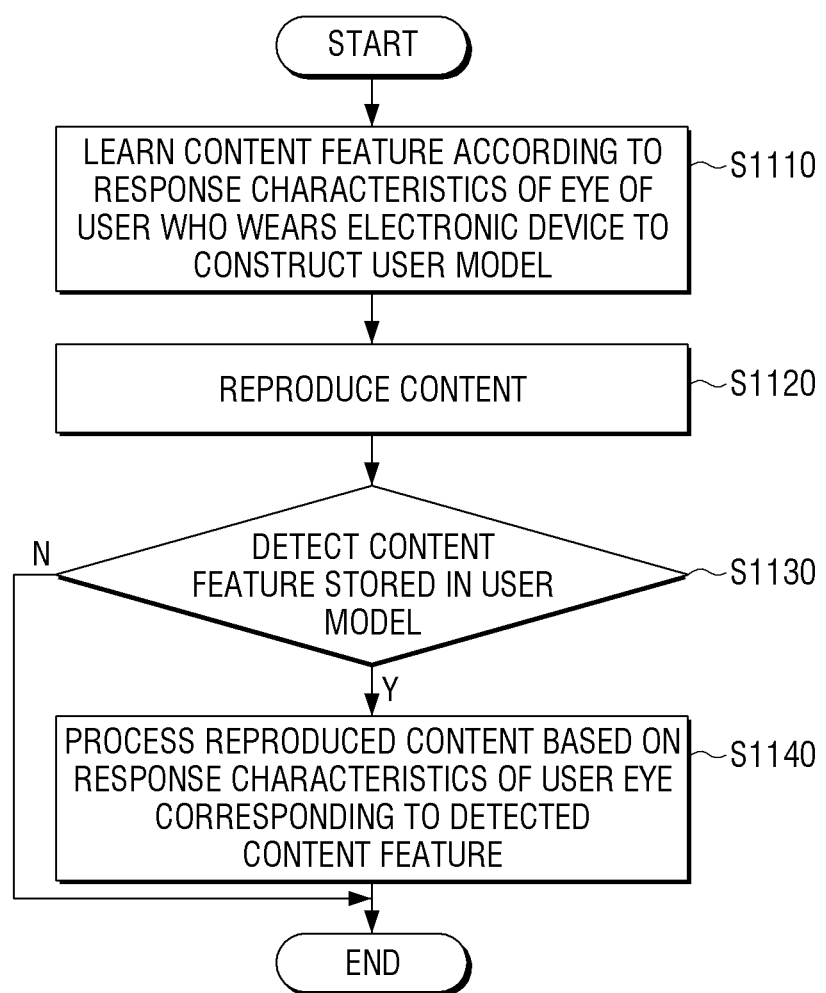
FIG. 11 is a flowchart of a method of controlling an electronic device according to an example embodiment of the present disclosure.

FIG. 11 is a flowchart of a method of controlling an electronic device according to an example embodiment of the present disclosure.

First, the electronic device 100 may learn a content feature according to response characteristics of an eye of a user who wears the electronic device 100 to construct a user model (S1110). In detail, the electronic device 100 may capture an image including the eye(s) of the user who wears an electronic device during reproduction of learning content and, upon detecting predetermined response characteristics of the user's eye(s) included in the image, the electronic device 100 may acquire a content feature included in a content frame within a predetermined content section from a time point at which the predetermined response characteristics are detected and may learn the predetermined response characteristics and the content feature to construct a user model.

The electronic device 100 may reproduce content (S1120).

The electronic device 100 may detect a content feature stored in the user model from the reproduced content (S1130). In detail, the electronic device 100 may analyze a content frame of a preceding content section of a currently reproduced content frame during reproduction of content to determine whether a content feature stored in the user model is present.

Upon detecting a content feature included in the user model (S1130-Y), the electronic device 100 may process reproduced content based on response characteristics of a user's eye(s) corresponding to the detected content feature (S1140). In detail, the electronic device 100 may process an image of a content frame including the detected content feature based on the detected content feature and response characteristics corresponding to the detected content feature. For example, the electronic device 100 may perform smoothing processing and filtering processing on a content frame including a content feature or may adjust a brightness change value or a saturation value.

According to the aforementioned various example embodiments of the present disclosure, an image of a content feature expressed as a user negative response may be processed and, thus, the user may view the image more conveniently without adverse stimulation.

Figure 12:
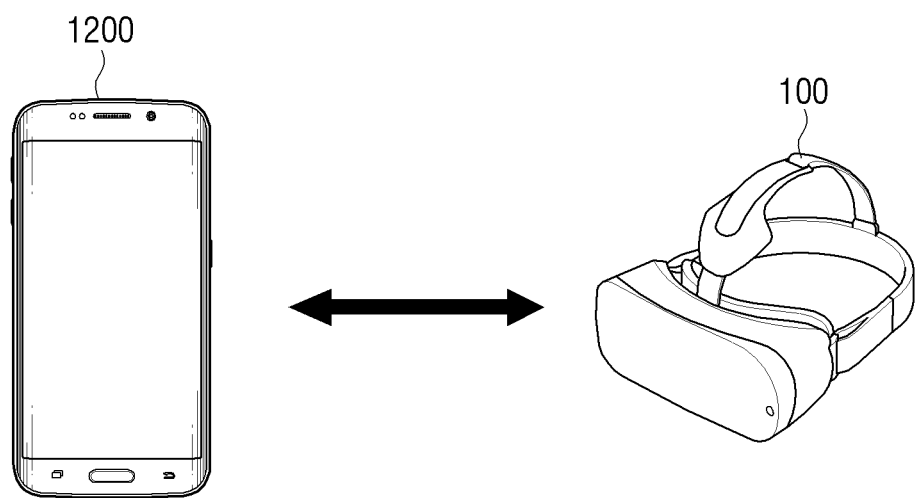
FIG. 12 is a diagram for explanation of a system including a portable terminal and an electronic device according to an example embodiment of the present disclosure.

According to the aforementioned example embodiments of the present disclosure, the electronic device 100 constructs a user model and processes content using the constructed user model, but these are merely example embodiments and, thus, as shown in FIG. 12, a portable terminal 1200 connected to the electronic device 100 may construct the user model and may process content using the constructed user model.

In detail, while the portable terminal 1200 transmits learning content to the electronic device 100 and the electronic device 100 reproduces the learning content, the electronic device 100 may photograph a user's eye(s) and may transmit the captured image data to the portable terminal 1200. In this case, upon detecting predetermined response characteristics of a user's eye(s), the electronic device 100 may transmit the captured image data to the portable terminal 1200.

The portable terminal 1200 may construct a user model for storing response characteristics of a user's eye(s) and a content feature corresponding thereto based on the learning content and the captured image data.

Upon transmitting content including a content feature included in the user model to the electronic device 100, the portable terminal 1200 may process an image of content based on a content feature included in the user model and response characteristics of a corresponding user's eye(s) and, then, may transmit the image-processed content to the electronic device 100.

Figure 13:
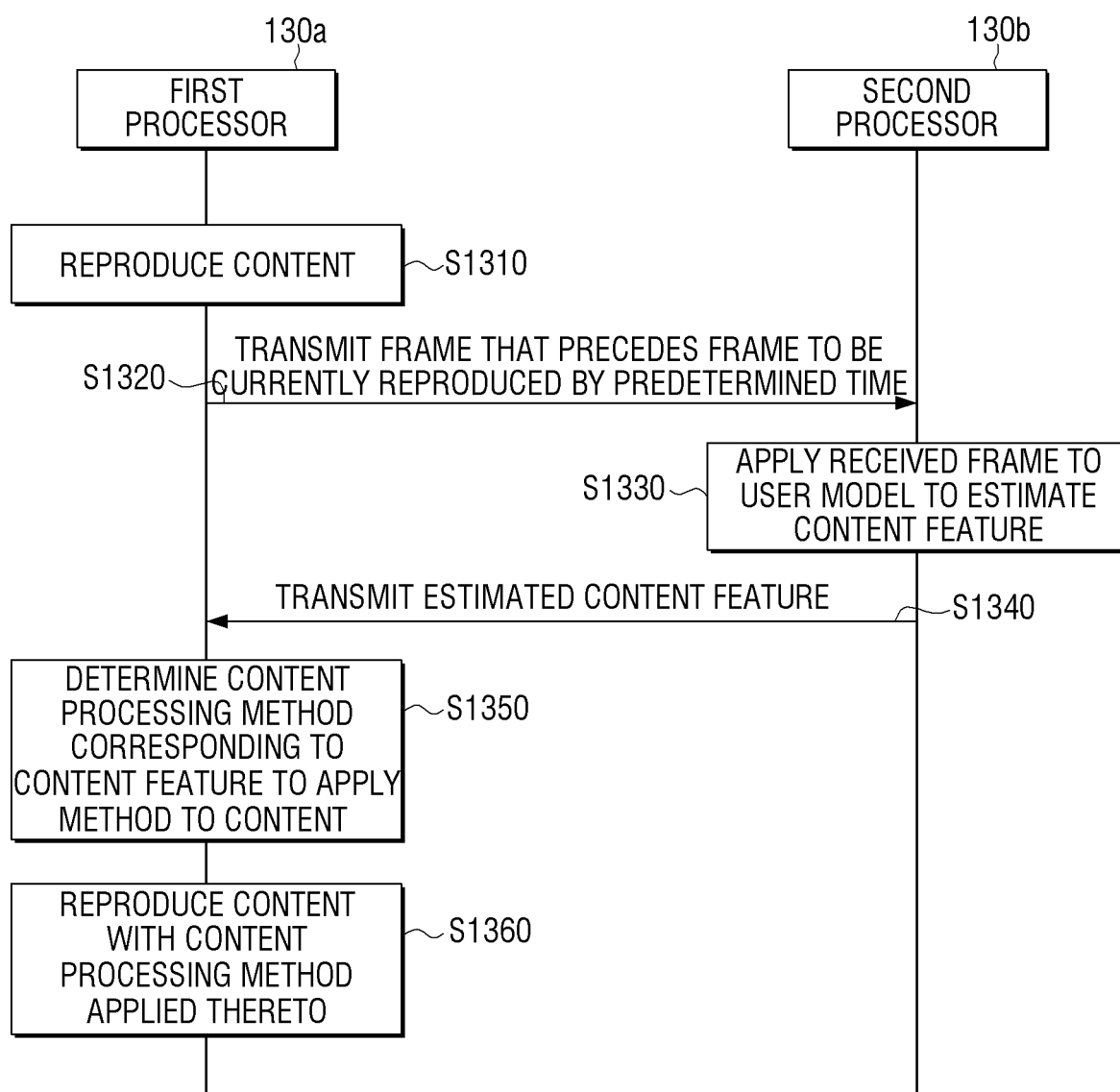
FIG. 13 is a flowchart for explanation of a case of estimating a content feature when an electronic device includes a first processor and a second processor according to an example embodiment of the present disclosure.

FIG. 13 is a flowchart used for explaining of a case of estimating a content feature when an electronic device includes a first processor and a second processor according to an example embodiment of the present disclosure.

Referring to FIG. 13, the electronic device 100 may include a first processor 130a and a second processor 130b.

The first processor 130a may control execution of at least one of application installed in the electronic device 100 and may perform graphic processing on an image (e.g., a live view image, a captured image, and a video image) acquired by the electronic device 100. The first processor 130a may be implemented in the form of a system on chip (SoC) formed by integrating functions of a central processing unit (CPU), a graphic processing unit (GPU), a communication chip, a sensor, and so on. The first processor 130a may also be referred to as an application processor (AP) in the present disclosure.

The second processor 130b may estimate an interest region of an image using a data recognition model.

The second processor 130b may be manufactured in the form of a dedicated hardware chip for artificial intelligence (AI) for performing a function of estimating an interest region using the data recognition model. According to various example embodiments of the present disclosure, in the case of a data recognition model using visual understanding as a core technology, the dedicated hardware chip for artificial intelligence (AI) may include a GPU.

The electronic device 100 may further include a third processor, a fourth processor, and so on, for performing the same function(s) as the second processor 130b.

According to various example embodiments of the present disclosure, a function performed by the first processor 130a may be stored in the memory 140 and may correspond to an application for performing various functions, and a function performed by the second processor 130b may correspond to an OS of the electronic device 100.

For example, a camera application may generate a live view image and may determine a data recognition model corresponding to a predetermined condition. The camera application may transmit information related to an interest region estimation request and a data recognition model determined with respect to an OS and/or a server positioned outside (external to) the electronic device 100.

The OS and/or the external server may estimate an interest region using the included data recognition model.

According to an example embodiment of the present disclosure, the first processor 130a may reproduce content (S1310).

For example, the first processor 130a may reproduce a video image(s) stored in a memory or may receive streaming video data from an external server and may reproduce the streaming the video data.

The first processor 130a may transmit a frame that precedes a frame to be currently reproduced by a predetermined time, to the second processor 130b (S1320).

The second processor 130b may apply the received frame to the user model to estimate a content feature included in a frame (S1330).

When a content feature is estimated, the second processor 130b may transmit the estimated content feature to the first processor 130a (S1340).

The first processor 130a may determine a content processing method corresponding to the estimated content feature and may apply the content processing method to content. For example, the first processor 130a may perform smoothing processing and filtering processing on a frame including a content feature or may adjust a brightness value or a saturation value (S1350).

The first processor may reproduce the content to which the content processing method is applied (S1360).

Figure 14:
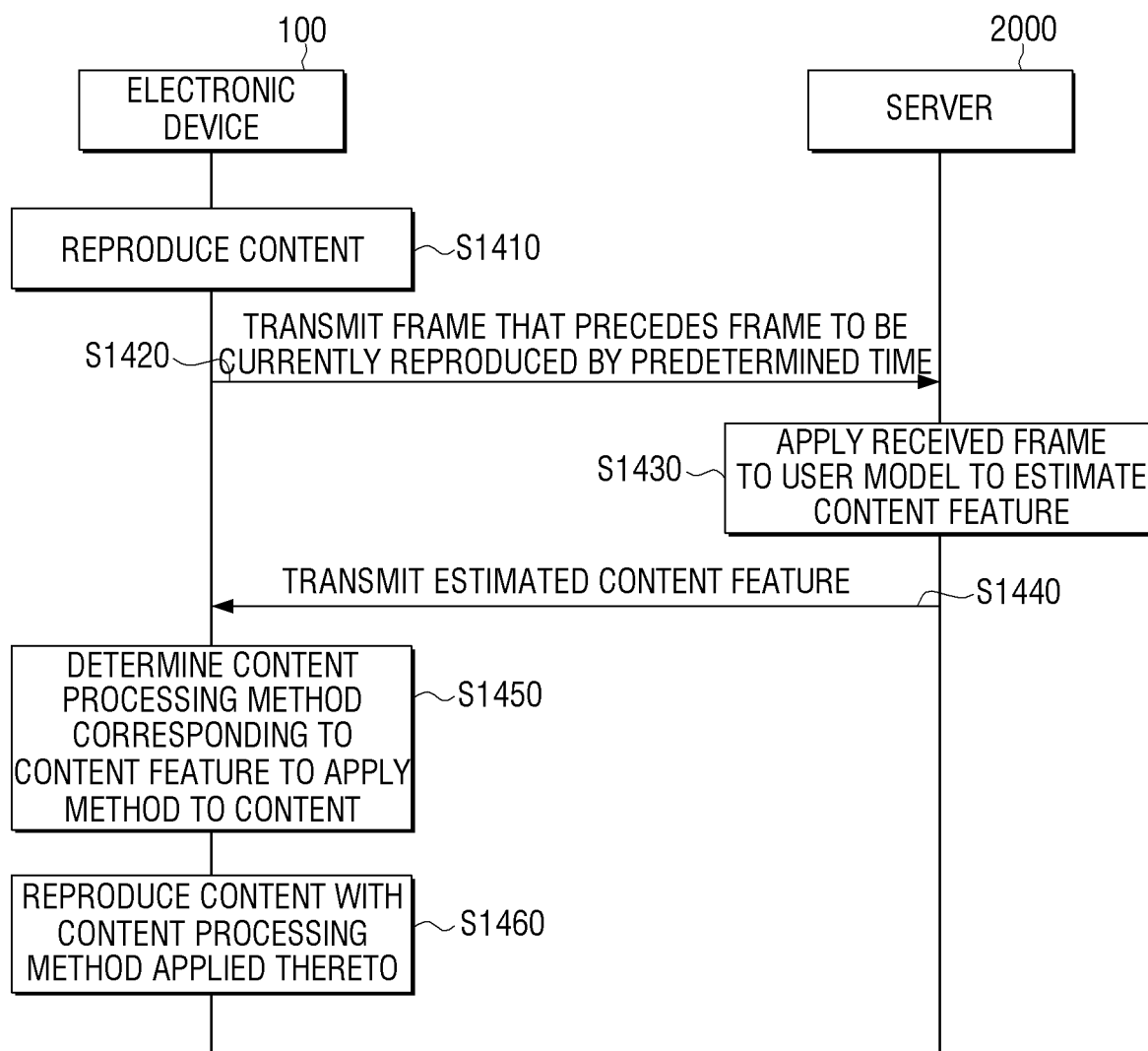
FIG. 14 is a flowchart for explanation of a case of estimating a content feature using a server by an electronic device according to an example embodiment of the present disclosure.

FIG. 14 is a flowchart used for explaining a case of estimating a content feature using a server by an electronic device according to an example embodiment of the present disclosure.

As described above with reference to FIG. 4B, the server 2000 according to an example embodiment of the present disclosure may include a user model.

According to an example embodiment of the present disclosure, the electronic device 100 may reproduce content (S1410).

For example, the electronic device 100 may reproduce a video image(s) stored in a memory or may receiving streaming video data from an external server and may reproduce the streaming video data.

The electronic device 100 may transmit a frame that precedes a frame to be currently reproduced by a predetermined time, to the server 2000 (S1420).

The server 2000 may apply the received frame to the user model to estimate a content feature included in the frame (S1430).

Upon estimating the content feature, the server 2000 may transmit the estimated content feature to the electronic device 100 (S1440).

The electronic device 100 may determine a content processing method corresponding to the estimated content feature and may apply the content processing method to content. For example, the electronic device 100 may perform smoothing processing or filtering processing on a frame included in a content feature or may adjust a brightness value or a saturation value (S1450).

The electronic device 100 may reproduce the content to which the content processing method is applied (S1460).

Figure 15:
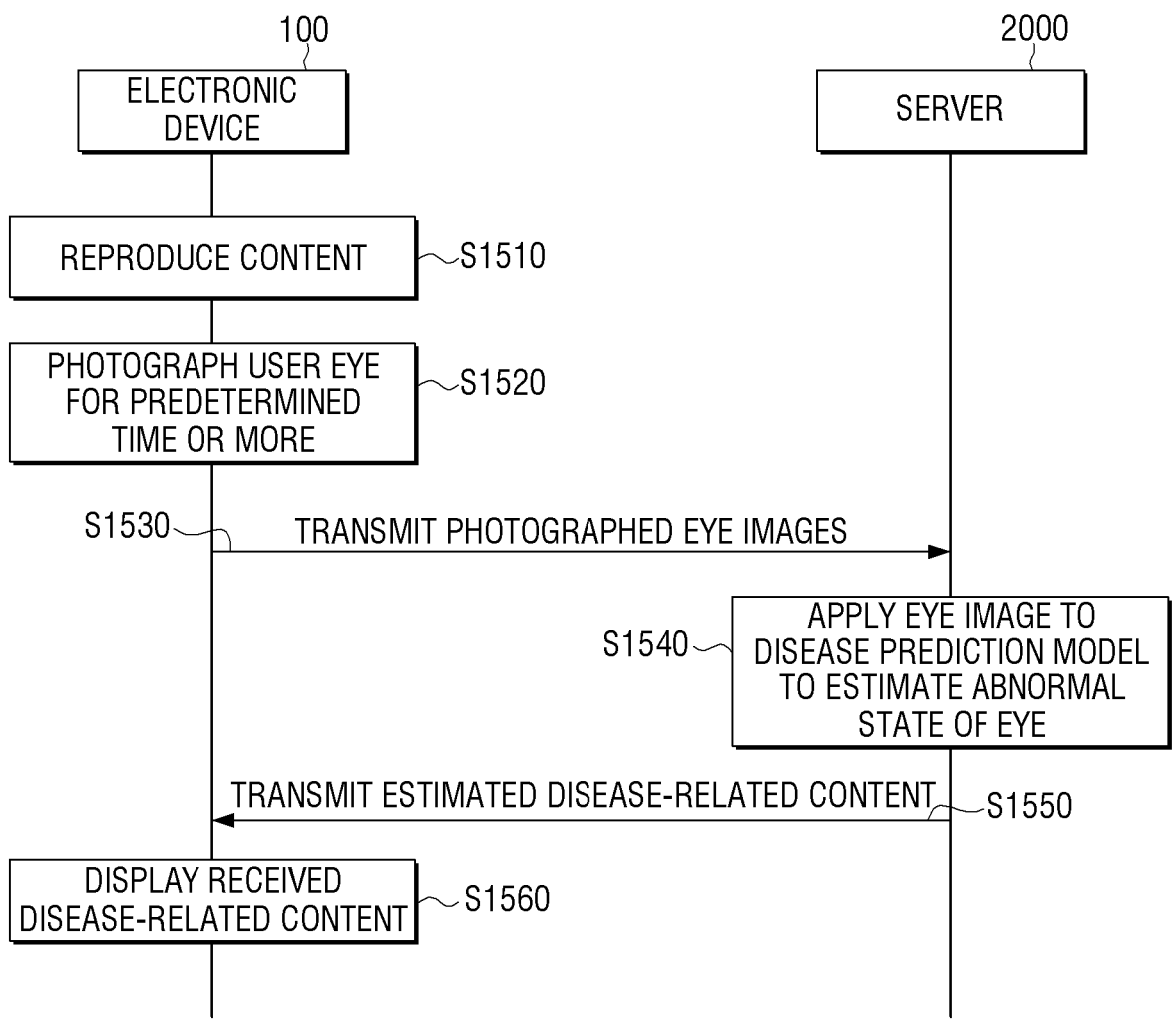
FIG. 15 is a flowchart for explanation of a case of estimating an abnormal state related to an eye using a server by an electronic device according to an example embodiment of the present disclosure.

FIG. 15 is a flowchart used for explaining a case of estimating an abnormal state related to an eye(s) using a server by an electronic device according to an example embodiment of the present disclosure.

According to an example embodiment of the present disclosure, the server 2000 may include a disease prediction model.

According to an example embodiment of the present disclosure, the electronic device 100 may reproduce content (S1510).

For example, the electronic device 100 may reproduce a video image(s) stored in a memory or may receive video data from an external server and may reproduce the video data.

The electronic device 100 may photograph a user's eye(s) for a predetermined time or more (S1520). For example, while a user views a video image, the electronic device 100 may photograph a user's eye(s) who views the video image, for about one hour. In addition, according to various example embodiments of the present disclosure, while a user views a video image, the electronic device 100 may photograph a user's eye(s) that views the video image for about 5 seconds and may repeatedly re-perform photographing for about five seconds after one minute intervals.

The electronic device 100 may transmit the photographed eye images to the server 2000 (S1530).

The server 2000 may apply the received eye images to the disease prediction model to estimate an abnormal state related to an eye(s) (S1540). For example, when the server 2000 applies an image(s) in which a surrounding area of a user's eye(s) becomes red to a disease prediction model, the disease prediction model may estimate that a user eye has iritis.

The server 2000 may transmit the estimated disease-related content to the electronic device 100 (S1550).

The electronic device 100 may displayed the received disease-related content (S1560). According to various example embodiments of the present disclosure, another electronic device (e.g., a smartphone and a tablet PC) that communicates with the electronic device 100 may display the received disease-related content.

The aforementioned methods can include a computer readable medium including program commands for executing operations implemented using various computers. The computer readable medium can store program commands, data files, data structures or combinations thereof. The program commands recorded in the medium may be specially designed and configured for the present disclosure or be known to those skilled in the field of computer software. Examples of a computer readable recording medium include magnetic media such as hard discs, floppy discs and magnetic tapes, optical media such as CD-ROMs and DVDs, magneto-optical media such as floptical discs, or hardware devices such as ROMs, RAMs and flash memories, which are specially configured to store and execute program commands. Examples of the program commands include machine language code created by a compiler and high-level language code executable by a computer using an interpreter and the like. The hardware device may be configured to operate as one or more software modules to perform an operation according to the present disclosure, or vice versa.

The example embodiments may be implemented in software program including commands stored in a computer-readable storage medium (or media).

The computer may be a device that is capable of calling a command stored in a storage medium and performing an operation according to the example embodiments of the present disclosure according to the called command and may include electronic devices according to the example embodiments of the present disclosure.

The computer-readable storage medium may be provided in the form of a non-transitory storage medium. Here, the term 'non-transitory' may indicate that a storage medium does not include a signal and is tangible.

The control method according to the example embodiments of the present disclosure may be included in a computer program product. The computer program product may be traded between a seller and purchaser.

The computer program product may include an software program and a computer readable medium (or media) having recorded thereon the software program. For example, the computer program product may include a software program type of product (e.g., a downloadable app) that is electronically distributed through a manufacturer or an E-market (e.g., a Google player store and an app store) of the electronic device. For electronic distribution, at least a portion of a software program may be stored in a storage medium or may be temporally generated. In this case, the storage medium may be a server of a manufacturer, a server of an E-market, or a storage medium of a relay server for temporally storing a software program.

The computer program product may include a storage medium of a server or a storage medium of an electronic device in a system including a server and an electronic device. In addition, when a third device (e.g., a smartphone) communication-connected to a server or an electronic device is present, the computer program product may include a storage medium of the third device. The computer program product may be transmitted to an electronic device or a third device from a server or may include a software program transmitted to the electronic device from the third device.

In this case, one of a server, an electronic device, and a third device may execute the computer program product to perform the methods according to the aforementioned example embodiments of the present disclosure. Alternatively, two or more of the electronic device and the third device may execute the computer program product to distribute and implement the method according to the aforementioned example embodiments of the present disclosure.

For example, a server (e.g., a cloud server or an artificial intelligence (AI) server) may execute the computer program product stored in the server and an electronic device that is communication-connected to the server may be controlled to perform the methods according to the example embodiments of the present disclosure.

As another example, the third device may execute the computer program product and the electronic device that is communication-connected to the third device may be controlled to perform the methods according to the example embodiments of the present disclosure. When the third device executes the computer program product, the third device may download the computer program product from the server and may execute the downloaded computer program product. The third device may execute the computer program product provided in a preloaded state to perform the method according to the example embodiments of the present disclosure.

The foregoing example embodiments and advantages are merely examples and are not to be construed as limiting the present disclosure. The present teaching can be readily applied to other types of apparatuses. Also, the description of the example embodiments of the present disclosure is intended to be illustrative, and not to limit the scope of the claims, and many alternatives, modifications, and variations will be apparent to those skilled in the art.

What is claimed is:

1. A method of controlling an electronic device worn by a user to provide images, the method comprising:
    constructing, by training, a user model in which one or more content features are each stored in association with a corresponding response characteristic of an eye of a user wearing the electronic device;
    detecting content features in content during reproduction of the content for perception by the user;
    in response to detecting, by the content feature detecting, of a content feature reflected in the user model, identifying the response characteristic of the eye of the user corresponding to the detected content feature, using the user model; and
    controlling the reproduction of the content for perception by the user according to a content reproduction control method based on the identified response characteristic of the eye of the user,
    wherein the detecting of content features in content comprises analyzing a preceding content section of a currently reproduced content during the reproduction for perception by the user of the currently reproduced content to analyze whether a content feature reflected in the user model is present in the preceding content section, and
    wherein the content reproduction control method is determined based on a control model in which response characteristics of the eye of the user are stored in association with content reproduction control methods.

2. The method as claimed in claim 1, wherein the constructing of the user model comprises:
    capturing images including the eye of the user wearing the electronic device during reproduction of training content;
    in response to detecting a predetermined response characteristic of the eye of the user included in one or more of the captured images, acquiring a content feature included in a content frame within a content section of the training content relative to a time point at which the predetermined response characteristic is detected; and
    constructing the user model by associating the predetermined response characteristic and the acquired content feature.

3. The method as claimed in claim 2, wherein the acquired content feature comprises at least one of an object included in the content frame within the content section, a brightness change of the content frame, or a color change of the content frame.

4. The method as claimed in claim 1, wherein the controlling of the reproduction of the content comprises:
    in response to detecting, in the content, a first content feature reflected in the user model, controlling the reproduction of the content by processing an image of a content frame comprising the first content feature according to a content reproduction control method determined based on the response characteristic of the eye of the user identified as corresponding to the first content feature.

5. The method as claimed in claim 4, wherein the controlling of the reproduction of the content comprises:
    based on the first content feature being a specific object and the identified response characteristic in the user model of the specific object corresponding to a negative response, performing a content reproduction control method for filtering processing or smoothing processing on the object included in the content.

6. The method as claimed in claim 4, wherein the controlling of the reproduction of the content comprises:
    based on the first content feature being a specific brightness change and the identified response characteristic in the user model to the specific brightness change corresponding to a negative response, performing a content reproduction control method for adjusting a change amount of the specific brightness change.

7. The method as claimed in claim 4, wherein the controlling of the reproduction of the content comprises:
    based on the first content feature being a specific color change and the identified response characteristic in the user model to the specific color change corresponding to a negative response, performing a content reproduction control method for adjusting a saturation value of the specific color change.

8. The method as claimed in claim 2, further comprising:
    based on identifying that the response characteristic in the user model to a particular content feature corresponds to a positive response, acquiring a keyword associated with the particular content feature; and
    providing a list comprising recommended content determined based on the acquired keyword.

9. The method as claimed in claim 1, further comprising:
    cumulatively storing captured images including the eye of the user;
    analyzing the stored images to determine whether an abnormal state of the eye of the user is identified; and
    based on determining that an abnormal state of the eye of the user is identified, providing information relating to the abnormal state.

10. An electronic device worn by a user to provide images, comprising:
    a display;
    a camera;
    a memory; and
    a processor configured to:
        construct, by training, a user model, for storage in the memory, in which one or more content features are each associated with a corresponding response characteristic of an eye of user wearing the electronic device;
detect content features in content during reproduction of the content for perception by the user;
in response to detecting, by the content feature detecting, of a content feature reflected in the user model, identify the response characteristic of the eye of the user corresponding to the detected content feature, using the user model; and
control reproduction of the content for perception by the user according to a content reproduction control method based on the identified response characteristic of the eye of the user,
wherein the detecting of content features in content comprises analyzing a preceding content section of a currently reproduced content during the reproduction for perception by the user of the currently reproduced content to analyze whether a content feature reflected in the user model is present in the preceding content section, and
wherein the content reproduction control method is determined based on a control model in which response characteristics of the eye of the user are stored in association with content reproduction control methods.

11. The electronic device as claimed in claim 10, wherein the processor is further configured to:
control the camera to capture images including the eye of the user wearing the electronic device during reproduction of training content;
in response to detecting a predetermined response characteristic of the eye of the user included in one or more of the captured images, acquire a content feature included in a content frame within a content section of the training content relative to a time point at which the predetermined response characteristic is detected; and
construct the user model by associating the predetermined response characteristic and the acquired content feature.

12. The electronic device as claimed in claim 11, wherein the acquired content feature comprises at least one of an object included in the content frame within the content section, a brightness change of the content frame, or a color change of the content frame.

13. The electronic device as claimed in claim 10, wherein the processor is configured to, in response to detecting, in the content, a first content feature reflected in the user model, control the reproduction of the content by processing an image of a content frame comprising the first content feature according to a content reproduction control method determined based on the response characteristic of the eye of the user identified as corresponding to the first content feature.

14. The electronic device as claimed in claim 13, wherein the processor is configured to, based on the first content feature being a specific object and the identified response characteristic in the user model of the specific object corresponding to a negative response, control the reproduction of the content by performing a content reproduction control method for filtering processing or smoothing processing on the object included in the content.

15. The electronic device as claimed in claim 13, wherein the processor is configured to, based on the first content feature being a specific brightness change and the identified response characteristic in the user model to the specific brightness change corresponding to a negative response, control the reproduction of the content by performing a content reproduction control method for adjusting a change amount of the specific brightness change.

16. The electronic device as claimed in claim 13, wherein the processor is configured to, based on the first content feature being a specific color change and the identified response characteristic in the user model to the specific color change corresponding to a negative response, control the reproduction of the content by performing a content reproduction control method for adjusting a saturation value of the specific color change.

17. The electronic device as claimed in claim 11, wherein the processor is configured to:
based on identifying that the response characteristic in the user model to a particular content feature corresponds to a positive response, acquire a keyword associated with the particular content feature; and
provide a list comprising a recommended content determined based on the acquired keyword.

18. The electronic device as claimed in claim 10, wherein the processor is configured to:
cumulatively store captured images including the eye of the user;
analyze the stored images to determine whether an abnormal state of the eye of the user is identified; and
based on determining that an abnormal state of the eye of the user is identified, provide information relating to the abnormal state.

* * * * *